United States Patent
Corey et al.

(10) Patent No.: US 10,529,450 B2
(45) Date of Patent: Jan. 7, 2020

(54) REAL-TIME PHASE DETECTION OF FREQUENCY BAND

(71) Applicant: Medtronic, Inc., Minneapolis, MN (US)

(72) Inventors: Robert A. Corey, Arden Hills, MN (US); Gregory J. Loxtercamp, Edina, MN (US); Heather Diane Orser, Farmington, MN (US); Scott R. Stanslaski, Shoreview, MN (US); Jadin C. Jackson, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/057,417

(22) Filed: Aug. 7, 2018

(65) Prior Publication Data

US 2018/0350465 A1    Dec. 6, 2018

Related U.S. Application Data

(63) Continuation of application No. 14/945,139, filed on Nov. 18, 2015, now Pat. No. 10,095,837.

(60) Provisional application No. 62/114,650, filed on Feb. 11, 2015, provisional application No. 62/083,038, filed on Nov. 21, 2014.

(51) Int. Cl.
| | |
|---|---|
| *G16H 40/63* | (2018.01) |
| *A61B 5/048* | (2006.01) |
| *A61B 5/04* | (2006.01) |
| *A61B 5/00* | (2006.01) |

(52) U.S. Cl.
CPC .............. *G16H 40/63* (2018.01); *A61B 5/048* (2013.01); *A61B 5/04014* (2013.01); *A61B 5/4836* (2013.01); *A61B 5/4088* (2013.01); *A61B 5/4094* (2013.01); *A61B 5/4839* (2013.01); *A61B 5/686* (2013.01); *A61B 5/7246* (2013.01); *A61B 5/7257* (2013.01)

(58) Field of Classification Search
CPC ... A61B 5/048; A61B 5/4836; A61B 5/04014; A61B 5/4839; A61B 5/7257; A61B 5/7246; A61B 5/686; A61B 5/4088; A61B 5/4094; G16H 40/63

See application file for complete search history.

(56) References Cited

U.S. PATENT DOCUMENTS

| | | |
|---|---|---|
| 4,445,512 A | 5/1984 | Krupka et al. |
| 6,711,547 B1 | 3/2004 | Glover |
| 7,231,258 B2 | 6/2007 | Moore et al. |
| 7,548,787 B2 | 6/2009 | Feher |
| 8,639,335 B2 | 1/2014 | Peichel et al. |

(Continued)

OTHER PUBLICATIONS

Anderson et al., "Phase-dependent stimulation efects on bursting activity in a neural network cortical simulation," National Institutes of Health, vol. 84 (1), NIH Public Access, Mar. 2009, 23 pp.

(Continued)

*Primary Examiner* — Vongsavanh Sengdara
(74) *Attorney, Agent, or Firm* — Shumaker & Sieffert, P.A.

(57) ABSTRACT

Techniques are described for real-time phase detection. For the phase detection, a signal is correlated with a frequency component of a frequency band whose phase is being detected, and the correlation includes predominantly decreasing weighting of past portions of the signals.

20 Claims, 10 Drawing Sheets

(56) References Cited

U.S. PATENT DOCUMENTS

| | | | |
|---|---|---|---|
| 9,572,737 B2 | 2/2017 | McNeely et al. | |
| 9,619,621 B2 | 4/2017 | Dicks et al. | |
| 9,666,061 B2 | 5/2017 | Reeder et al. | |
| 9,813,270 B2 | 11/2017 | Feher | |
| 10,095,837 B2 | 10/2018 | Corey et al. | |
| 2002/0128563 A1 | 9/2002 | Carlson et al. | |
| 2004/0073098 A1 | 5/2004 | Geva et al. | |
| 2005/0075067 A1 | 4/2005 | Lawson et al. | |
| 2006/0025824 A1 | 2/2006 | Freeman et al. | |
| 2006/0224191 A1 | 10/2006 | Dilorenzo | |
| 2007/0123758 A1 | 5/2007 | Miesel et al. | |
| 2007/0265669 A1* | 11/2007 | Roline | A61N 1/36564 607/6 |
| 2007/0266778 A1 | 11/2007 | Corey et al. | |
| 2008/0083414 A1 | 4/2008 | Messerges | |
| 2009/0264956 A1* | 10/2009 | Rise | A61N 1/36082 607/45 |
| 2009/0264967 A1* | 10/2009 | Giftakis | A61N 1/36082 607/62 |
| 2010/0029284 A1 | 2/2010 | Feher | |
| 2010/0036269 A1 | 2/2010 | Ferren et al. | |
| 2010/0076514 A1* | 3/2010 | Cho | A61B 5/0031 607/18 |
| 2010/0100153 A1* | 4/2010 | Carlson | A61N 1/0529 607/45 |
| 2010/0249627 A1* | 9/2010 | Zhang | A61B 5/0452 600/518 |
| 2011/0190850 A1* | 8/2011 | Reinke | A61N 1/37288 607/60 |
| 2012/0154582 A1* | 6/2012 | Johnson | G06F 19/321 348/143 |
| 2013/0172774 A1 | 7/2013 | Crowder et al. | |
| 2013/0218232 A1 | 8/2013 | Giftakis et al. | |
| 2014/0319921 A1 | 10/2014 | Lisi et al. | |
| 2014/0359508 A1 | 12/2014 | Otero Diaz et al. | |
| 2016/0342752 A1 | 11/2016 | Stueckemann et al. | |
| 2017/0079585 A1 | 3/2017 | Ney et al. | |
| 2017/0188993 A1 | 7/2017 | Hamilton et al. | |

OTHER PUBLICATIONS

Bi et al., "Synaptic Modifications in Cultured Hippocampal Neurons: Dependence on Spike Timing, Synatpic Strength, and Postsynaptic Cell Type," The Journal of Neuroscience, vol. 18 (24), Dec. 15, 1998, 9 pp.

Bliss et al., "Long-Lasting potentiation of Synaptic Transmission in the Dentate Area of the Anaesthetized Rabbit Following Stimulation of the Perforant Path," National Institute for Medical Research, 232, Feb. 12, 1973, 26 pp.

Canolty et al., "High Gamma Power Is Phase-Locked to Theta Oscillations in Human Neocortex," Science, vol. 313, Sep. 15, 2006, 4 pp.

Canolty et al., "The functional role of cross-frequency coupling," Trends in Cognitive Sciences, vol. 14, No. 11, Nov. 2010, Elsevier Ltd, 10 pp.

Chen et al., "Real-Time Brain Oscillation Detection and Phase-Locked Stimulation Using Autoregressive Spectral Estimation and Time-Series Forward Prediction," Biomedical Engineering, vol. 60 Issue 3, IEEE, Published Jan. 31, 2011, Date of current version Mar. 11, 2013, 10 pp.

Chen et al., "Real-Time Brain Oscillation Detection and Phase-Locked Stimulation Using Autoregressive Spectral Estimation and Time-Series Forward Prediction," National Institutes of Health, IEEE Trans Biomed Eng, 60 (3), Mar. 2013, 25 pp.

Cole, "Rectification and Inductance in the Squid Giant Axon," College pf Physicians and Surgeons, Retrieved from ipg.rupress.org, Mar. 14, 1941, published Sep. 20, 1941, 23 pp.

Colgin et al., "Gamma Oscillations in the Hippocampus," Physiology, vol. 25, Oct. 2010, 11 pp.

Da Silva, EEG Analysis: Theor and Practice, Chapter 54 Part IX, Computer-Assisted EEG Analysis, Electroencephalography: Basic Principals, clinical applications and related fields., Lippincott, Williams and Wilkins, Sixth Edition, 2005, 31 pp.

Da Silva, "Neurocognitive Processes and the EEG/MEG," Chapter 50 Part VII, Evoked Potentials and Event—Related EEG Phenomena,Electroencephalography: Basic Principals, clinical applications and related fields., Lippincott, Williams and Wilkins, Sixth Edition, 2005, 30 pp.

Daitch et al., "Frequency-specific machanism links human brain networks for spatial attention," Proceedings of the National Academy of Sciences (PNAS), vol. 110 No. 48, Nov. 26, 2013, 6 pp.

Fell et al., "Phase-locking within Human Mediotemporal lobe predicts memory formation," NeuroImage, vol. 43, No. 2, Elsevier, Jul. 22, 2008, 10 pp.

Fell et al., "The role of phase synchronization in memory processes," Nature Review, Neuroscience, vol. 12, No. 2 Macmillan Publishers Limited, Feb. 2011, 15 pp.

Hanslmayr et al., "Prestimulus Oscillatory Phase at 7 Hz Gates Cortical Information Flow and Visual Perception," Current Biology vol. 23, No. 2 Elsevier Ltd, Oct. 31, 2013, 6 pp.

Holscher et al., "Stimulation on the Positive Phase of Hippocampal Theta Rhythm Induces Long-Term Potentiation that Can Be Depotentiated by Stimulation on the Negative Phase in Area CA1 in Vivo," The Journal of Neuroscience, 17 (16), Aug. 15, 1997, 8 pp.

Hutcheon et al., "Resonance, Oscillation and the Intrinsic Frequency Preferences of Neurons," TINS vol. 23, No. 5, Elsevier Science Ltd., available online May 3, 2000, 7 pp.

Hyman et al., "Stimulation in Hippocampal Region CA1 in Behaving Rats Yields Long-Term Potentiation when delivered to the Peak of Theta and Long-Term Depression when Delivered to the Trough," The Journal of Neuroscience, 23 (37), Dec. 17, 2003, 7 pp.

Jackson et al., "Computationally efficient, configurable, causal, real-time phase detection applied to local filed potential oscillations," Neuromodulation Divsion, Medtronic Inc, Conference of Neural Engineering, 7 International IEEE/EMBS, Apr. 22-24, 2015, 6 pp.

Jacobs et al., "Brain Oscillations Control Timing of single-Neuron Activity in Humans," The Journal of Neuroscience, 27 (14), Apr. 4, 2007, 6 pp.

Lebedev et al., "Brain-machine interfaces: past, present and future," Trends in Neurosciences, vol. 29 No. 9, Science Direct, Jul. 21, 2006, 11 pp.

Lega et al., "Human Hippocampal Theta Oscillations and the Formation of Episodic Memories," Hippocampus, vol. 22, No. 4, Apr. 27, 2011, 14 pp.

Niedermeyer et al., "Normal EEG and Sleep: Adults and Elderly," Chapter 11 Part II, Normal EEG, Electroencephalography: Basic Principals, clinical applications and related fields., Lippincott, Williams and Wilkins, Sixth Edition, 2005, 32 pp.

Pavlides et al., "Long-term potentiation in the dentate gyrus is induced preferentially on the positive phase of 0 rhythm," Brain Research, Elsevier, vol. 439 No. 1/2, published, Mar. 1988, accepted Oct. 6, 1987, 7 pp.

Pfurtscheller et al., EEG Event-Related Desynchronization (ERD) and Event—Related Synchronizations (ERS), Chapter 45 Part VII, Evoked Potentials and Event—Related EEG Phenomena, Electroencephalography: Basic Principals, clinical applications and related fields., Lippincott, Williams and Wilkins, Sixth Edition, 2005, 14 pp.

Puil et al., "Quantification of Membrane Properties of trigeminal Root Ganglion Neurons in Guinea Pigs," Journal of Neurophyiology, vol. 55 No. 5, The American Physiological Society, May 1986, 22 pp.

Rizzuto et al., "Human neocortical oscillations exhibit theta phase differences between encoding and retrieval," NeuroImage, Science Direct, Elsevier, Mar. 15, 2006, 7 pp.

Rutishauser et al., "Human Memory Strength is Predicted by Theta-frequency phase-locking of single neurons," Nature Publishing Group, vol. 464, Apr. 8, 2010, 8 pp.

Sauseng et al., "What does phase information of oscillatory brain activity tell us about cognitive processes?," Science Direct, vol. 34, Elsevier Ltd., Mar. 29, 2008, 13 pp.

(56) References Cited

OTHER PUBLICATIONS

Van Zaen et al., "Adaptive tracking of EEG oscillations," Journal of Neuroscience Methods 186, Elsevier B.V. Oct. 23, 2009, 10 pp.
Prosecution History from U.S. Appl. No. 14/945,139, dated Dec. 5, 2017 through Jun. 1, 2018, 57 pp.

* cited by examiner

```
┌─────────────────────────────────────────────────────┐
│ DETERMINE PHASES FOR EACH OF ONE OR MORE FREQUENCY  │──100
│ COMPONENTS BASED ON WEIGHTING PRESENT AND MORE      │
│ RECENT SAMPLES MORE HEAVILY THAN EARLIER PORTIONS OF│
│                    THE SIGNAL                        │
└─────────────────────────────────────────────────────┘
                          │
                          ▼
┌─────────────────────────────────────────────────────┐
│ DETERMINE A PHASE OF FREQUENCY BAND BASED ON        │──102
│ DETERMINED PHASES FOR EACH OF THE ONE OR MORE       │
│              FREQUENCY COMPONENTS                    │
└─────────────────────────────────────────────────────┘
```

FIG. 6

```
┌─────────────────────────────────────────────────────┐
│  RECEIVE FIRST SIGNAL GENERATED FROM SECOND SIGNAL  │──104
└─────────────────────────────────────────────────────┘
                          │
                          ▼
┌─────────────────────────────────────────────────────┐
│ CORRELATE FIRST SIGNAL WITH FREQUENCY COMPONENT OF  │
│ FREQUENCY BAND OF THE SECOND SIGNAL BY PREDOMINATELY│──106
│ DECREASING WEIGHTING OF PAST PORTIONS OF FIRST SIGNAL│
└─────────────────────────────────────────────────────┘
                          │
                          ▼
┌─────────────────────────────────────────────────────┐
│  DETERMINE PHASE OF FREQUENCY COMPONENT BASED ON    │──108
│    FILTERED SIGNAL OUTPUTTED FROM THE CORRELATION   │
└─────────────────────────────────────────────────────┘
                          │
                          ▼
┌─────────────────────────────────────────────────────┐
│  DETERMINE PHASE OF FREQUENCY BAND BASED ON THE     │──110
│  DETERMINED PHASE OF THE FREQUENCY COMPONENT        │
└─────────────────────────────────────────────────────┘
```

FIG. 7

REAL-TIME PHASE DETECTION OF FREQUENCY BAND

This application is a continuation of U.S. patent application Ser. No. 14/945,139, filed Nov. 18, 2015, which claims the benefit of U.S. Provisional Application No. 62/083,038, filed Nov. 21, 2014, and U.S. Provisional Application No. 62/114,650, filed Feb. 11, 2015. The entire content of each of these applications is incorporated herein by reference.

GOVERNMENT INTEREST

This invention was made with government interest under prime award number N66001-14-2-4-31, subaward number 56400 awarded by DARPA. The government has certain rights in the invention.

TECHNICAL FIELD

The disclosure relates to phase detection, and more particularly, to phase detection for use in controlling medical therapy.

BACKGROUND

Medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an electrical stimulator delivers electrical therapy to a target tissue site within a patient with the aid of one or more electrodes, which may be deployed by medical leads, on a housing of the electrical stimulator, or both. In addition to or instead of electrical stimulation therapy, a medical device may deliver a therapeutic agent to a target tissue site within a patient with the aid of one or more fluid delivery elements, such as a catheter or a therapeutic agent eluting patch.

Some medical devices are configured to sense a patient parameter, such as a bioelectrical brain signal. A sensed patient parameter may be used for various purposes, such as to control therapy delivery by a medical device.

SUMMARY

The disclosure describes example techniques for determining a phase of a frequency band of a signal, such as a bioelectrical brain signal. A frequency band phase detector may include one or more frequency component phase detectors, where each frequency component refers to a frequency within the frequency band. Each of the frequency component phase detectors may be configured to determine a phase of the frequency component by weighting more recent samples of the signal more heavily than later samples of the signal, as part of a correlation of the signal with the frequency component. The frequency band phase detector may average, and in some examples, generate a weighted average of, the determined phases by each of the one or more frequency component phase detectors to determine the phase of the frequency band of the signal.

In one example, the disclosure describes a method comprising receiving, with a processor of a medical device, a first signal generated from a second signal, correlating, with the processor of the medical device, the first signal with a frequency component of a frequency band of the second signal, wherein correlating includes predominantly decreasing weighting of past portions of the first signal, and wherein predominantly decreasing weighting of past portions of the first signal comprises predominantly weighting present and more recent portions of the first signal more heavily than earlier portions of the first signal, and wherein the frequency band includes one or more frequency components, determining, with the processor of the medical device, a phase of the frequency component based on a filtered signal outputted from the correlation, determining, with the processor of the medical device, a phase of the frequency band based on the determined phase of the frequency component, and instructing, with the processor of the medical device, a therapy module to deliver therapy based on the determined phase of the frequency band.

In one example, the disclosure describes a medical device comprising frequency band phase detector comprising a frequency component phase detector configured to receive a first signal generated from a second signal, correlate the first signal with a frequency component of a frequency band of the second signal, wherein to correlate, the frequency component phase detector is configured to predominantly decrease weighting of past portions of the first signal, wherein predominantly decreasing weighting of past portions of the first signal comprises predominantly weighting present and more recent portions of the first signal more heavily than earlier portions of the first signal, and wherein the frequency band includes one or more frequency components, and determine a phase of the frequency component based on a filtered signal outputted from the correlation, and an averager configured to determine a phase of the frequency band based on the determined phase of the frequency component, and a therapy module configured to deliver therapy based on the determined phase of the frequency band.

In one example, the disclosure describes a medical device comprising means for receiving a first signal generated from a second signal, means for correlating the first signal with a frequency component of a frequency band of the second signal, wherein correlating includes predominantly decreasing weighting of past portions of the first signal, and wherein predominantly decreasing weighting of past portions of the first signal comprises predominantly weighting present and more recent portions of the first signal more heavily than earlier portions of the first signal, and wherein the frequency band includes one or more frequency components, means for determining a phase of the frequency component based on a filtered signal outputted from the correlation, means for determining a phase of the frequency band based on the determined phase of the frequency component, and means for delivering therapy based on the determined phase of the frequency band.

In one example, the disclosure describes a computer-readable storage medium comprising instructions that when executed cause one or more processors of a medical device to receive a first signal generated from a second signal, correlate the first signal with a frequency component of a frequency band of the second signal, wherein correlating includes predominantly decreasing weighting of past portions of the first signal, and wherein predominantly decreasing weighting of past portions of the first signal comprises predominantly weighting present and more recent portions of the first signal more heavily than earlier portions of the first signal, and wherein the frequency band includes one or more frequency components, determine a phase of the frequency component based on a filtered signal outputted from the correlation, determine a phase of the frequency band based on the determined phase of the frequency component, and instruct a therapy module to deliver therapy based on the determined phase of the frequency band.

The details of one or more examples are set forth in the accompanying drawings and the description below. Other features, objects, and advantages will be apparent from the description and drawings, and from the claims.

BRIEF DESCRIPTION OF DRAWINGS

FIG. 6 is a flowchart illustrating a method in accordance with one or more example techniques described in this disclosure.

FIG. 7 is a flowchart illustrating a method in accordance with one or more example techniques described in this disclosure.

DETAILED DESCRIPTION

Figure 1:
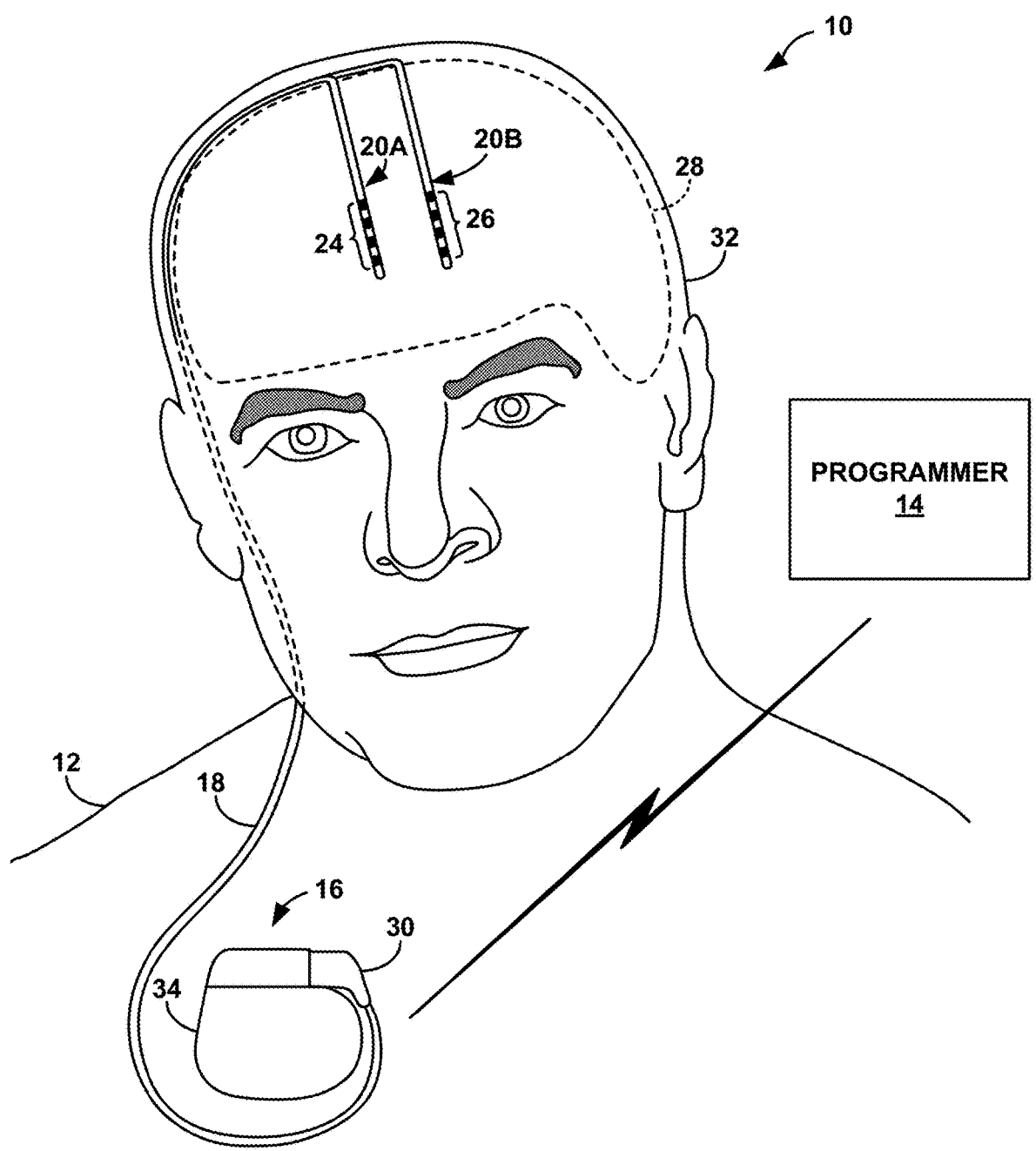
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example ways to determine phase of a frequency band within a signal. For purposes of illustration, the techniques described in this disclosure are described with respect to a frequency band of a bioelectrical brain signal, such as the theta wave with a frequency band from 4 Hertz (Hz) to 8 Hz. However, the techniques described in this disclosure are not so limited, and can be extended to other signals as well, such as signals from accelerometers or various other signals in which a phase of a frequency band is of interest. For ease, the examples are described for determining the phase of a theta wave.

Determining the phase of a frequency band may be useful for various purposes. As one example, delivery of medical therapy when the theta wave is at one phase may have different effect than delivery of medical therapy when the theta wave is at another phase. As another example, delivery of medical therapy at a phase of the theta wave other than the intended phase may result in less effective treatment.

In examples described in this disclosure, a frequency band phase detector that determines a phase of the frequency band may include one or more frequency component phase detectors, where each frequency component phase detector determines a phase of a frequency component within the frequency band. A frequency band phase detector may perform real-time Fourier transform (RTFT) may be considered as an RTFT block.

As an example, a frequency band phase detector for the frequency band from 4 Hz to 8 Hz may include three frequency component phase detectors. A first frequency component phase detector may determine the phase for the 4 Hz frequency component of the frequency band of the signal, a second frequency component phase detector may determine the phase for the 6 Hz frequency component of the frequency band of the signal, and a third frequency component phase detector may determine the phase for the 8 Hz frequency component of the frequency band of the signal. The 4 Hz, 6 Hz, and 8 Hz frequency components are provided for purposes of illustration only.

In some examples, the frequency band phase detector may include more or fewer frequency component phase detectors than three frequency component phase detectors. For example, if the frequency band includes only one frequency component, than only one frequency component phase detector may be utilized. To increase accuracy, the frequency band phase detector may include frequency component phase detectors at 1 Hz separation, rather than 2 Hz separation (e.g., frequency component phase detectors for 4 Hz, 5 Hz, 6 Hz, 7 Hz, and 8 Hz, and possibly even finer separation such as 0.5 Hz). Also, in the above example, the width of the frequency band is 4 Hz (8 Hz minus 4 Hz). As another example, if the frequency band were wider (e.g., more than 4 Hz), the frequency band phase detector may include more than three frequency component phase detectors.

In some examples, the number of frequency component phase detectors in the frequency band phase detector may be based on design of the frequency component phase detectors. As described below, each frequency component phase detector may include a "resonator," and if the tails of the resonator (e.g., the filtering provided by the resonators at frequencies other than the respective frequency component) is wide, then the frequency separation between frequency component phase detectors may be larger than if the tails of the resonator are narrower. For wide frequency separation, fewer frequency component phase detectors may be used, as compared to narrow frequency separation, where more frequency component phase detectors are used.

The frequency band phase detector may be configured to receive phase information of the respective frequency components from respective frequency component phase detectors. The frequency band phase detector may weight each of the phases, average the weighted phases, and output the result as phase information that indicates the phase of the frequency band of the signal.

Each frequency component phase detector may be configured to determine the phase of a respective frequency component by correlating the input signal with the frequency component for which it is configured, and weighing more recent portions of the signal more heavily than earlier portions of the signal, as part of the correlation. In other words, the effect of earlier portions of the signal is less than the effect of later portions of the signal in determining the phase of a frequency component of the signal. For example, each frequency component phase detector may include a weighted filter that filters the signal, based on respective frequency components of a frequency band, where the filtering includes correlating, with decreasing weighting of past portions of the signal, the signal with the frequency component. As described above, each frequency component phase detector may output phase information for the phases of respective frequency components, and the frequency band phase detector may determine a weighted average of each of the phases of the respective frequency components to determine the phase of the frequency band.

With the techniques described in this disclosure, it may be possible for the frequency band phase detector to almost instantaneously determine the current phase of the frequency band (e.g., real-time phase detection of the frequency band) with minimal power and circuit real-estate (e.g., negligible silicon area). Some other techniques for real-time phase detection do not rely on weighing more recent portions of the signal more heavily than earlier portions of the signal and averaging phases of frequency components of a frequency band for purposes of determining the phase of a frequency band. These other techniques may require a vast amount of power and circuit real-estate, which may not be available in medical devices such as implantable, wearable, or portable medical devices.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, nonrhythmic hyperkinesia, dystonia, tremor, and akinesia. In some cases, the movement disorder may be a symptom of Parkinson's disease or Huntington's disease. However, the movement disorder may be attributable to other patient conditions.

Although movement disorders are primarily referred to throughout the remainder of the application, in other examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 is also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28 (e.g., a tissue site under the dura mater of brain 28 or one or more branches or nodes, or a confluence of fiber tracks).

In some examples, leads 20 may be positioned to deliver therapy to a surface of brain 28 (e.g., the cortical surface of brain 28). For instance, IMD 16 may provide cortical stimulation therapy to patient 12 (e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

Although electrical stimulation therapy is primarily referred to throughout the remainder of the application, therapy system 10 may be configured to deliver other types of therapy in addition to or instead of electrical stimulation therapy, such as (e.g., drug delivery therapy). Moreover, for ease of description, the techniques described in this disclosure are described with respect to system 10 in which IMD 16 and leads 20A, 20B are implanted within the patient. However, the techniques described in this disclosure are not so limited. The techniques described in this disclosure may be applicable to implantable, wearable, and/or portable applications as well. Also, although the techniques are described with respect to medical devices, the techniques are not so limited and may be extended to non-medical devices as well.

In some examples, leads 20A, 20B may be implanted at other locations such as spinal cord, gastro, pelvic floor, peripheral nerve, etc. Also, there may be various therapies for different conditions such as pain, gastroparesis, obesity, urinary dysfunction, fecal dysfunction, or sexual dysfunction.

In the example shown in FIG. 1, IMD 16 may be implanted within a subcutaneous pocket in the pectoral region of patient 12. IMD 16 may be implanted within other regions of patient 12, such as a subcutaneous pocket in the chest, abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG2), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as the anterior thalamic nucleus, the internal capsule, the cingulate, the fornix, the mammillary bodies, the mammillothalamic tract (mammillothalamic fasciculus), and/or hippocampus, as a few examples. In the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as the frontal cortex, as one example, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. Leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage with or without multiple independent paths), pulse amplitude, pulse rate, pulse width, a waveform shape, and cycling parameters (e.g., with our without cycling, duration of cycling, and the like). In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In some examples, IMD 16 is configured to deliver electrical stimulation therapy to brain 28 of patient 12 in a closed loop manner or a pseudo-closed loop manner, in which IMD 16 controls the timing of the delivery of electrical stimulation to brain 28, the output parameters of the electrical stimulation, or both based on one or more of user input and input from a sensor. The sensor may, for example, provide feedback that may be used to control the electrical stimulation output from IMD 16.

In addition to being configured to deliver therapy to manage a disorder of patient 12, therapy system 10 is configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical brain signals via one or more of the electrodes 24, 26 that are also used to deliver electrical stimulation to brain 28. In some examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor bioelectrical brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes (e.g., scalp electrodes). Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example referred to herein for ease of description, the sensing module and therapy module of IMD 16 are enclosed within a common outer housing 34.

The bioelectrical brain signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

In examples described in this disclosure, IMD 16 is configured to determine a phase of a frequency band of a signal, such as a frequency band of a bioelectrical brain signal. The bioelectrical brain signal includes a plurality of different frequency bands that are each useful for different therapies. For example, the activity of a bioelectrical brain signal of a patient in a frequency band of interest that may be indicative of a patient state includes, for example, a spectral pattern of a bioelectrical brain signal, a power level of a bioelectrical brain signal in one or more frequency sub-bands (e.g., two or more frequency sub-bands) of a frequency band, or both. The patient state can be, for example, a patient disease state, a state in which a symptom of a patient condition is observed, or a patient state indicative of the efficacy of therapy delivery by a medical device or the efficacy of medication.

Different frequency bands of a bioelectrical brain signal are associated with different brain activity of the patient. One example of the frequency bands is shown in Table 1 below:

TABLE 1

| Frequency (f) Band Hertz (Hz) | Frequency Information |
| --- | --- |
| f < 4 Hz | δ (delta frequency band) |
| 4 Hz ≤ f < 8 Hz | theta frequency band |
| 8 Hz ≤ f < 13 Hz | α (alpha frequency band) |
| 13 Hz < f < 35 Hz | β (beta frequency band) |
| 35 Hz ≤ f < 100 Hz | γ (gamma frequency band) |
| 100 Hz < f < 400 Hz | high γ (high gamma frequency band) |

However, the frequency bands may have different frequency ranges than the example of Table 1. A frequency band may include (e.g., may be made up of) a plurality of frequency components, with a certain separation. As an illustrative example, the theta frequency band has a width of 4 Hz (8 Hz minus 4 Hz). In one example, the theta wave includes five frequency components with 1 Hz separation (e.g., 4 Hz, 5 Hz, 6 Hz, 7 Hz, and 8 Hz). In one example, the theta wave includes nine frequency components with 0.5 Hz separation (e.g., 4 Hz, 4.5 Hz, 5 Hz, 5.5 Hz, 6 Hz, 6.5 Hz, 7 Hz, 7.5 Hz, and 8 Hz). In one example, the theta wave includes three frequency components with 2 Hz separation (e.g., 4 Hz, 6 Hz, and 8 Hz). There may be an infinite number of frequency components in a frequency band with an infinitely small separation.

There may be various reasons for determining the phase of the frequency band of interest. For example, oscillatory rhythms in the brain are of great interest to the neuroscience, neurology, and neural interface communities; and a key signal characteristic emerging as at the focus of recent research is signal phase and phase locking. For instance, both neuronal phase locking and oscillatory phase locking within and across structures are correlated with memory strength and with attention and gaiting of information flow. Also, memory encoding may be separated from memory retrieval by the phase at which neurons fire, while phase coupling across frequencies and across brain structures has been strongly implicated in information transfer and processing within the brain. Many have reported the locking of high-frequency brain oscillations to specific phases of lower-frequency oscillations.

These phase-dependent mechanisms have been implicated in the coding of information, and the differential strengthening and weakening of neural connections with brain networks. It has been shown that electrical stimulation at the peak of a hippocampal theta wave induces long-term potentiation (synaptic strengthening) while stimulation applied to the trough induces long term synaptic depression: two changes thought to be related to memory storage in neural systems. Furthermore, some studies describe simulation studies that demonstrate phase dependent differences in stimulation effects, with the highest effectiveness of stimulation occurring at the peak the simulated network's bursting phase, resulting in reduction or elimination of burst firing. Thus, phase dependence with respect to local network oscillations appears to affect both neuronal connectivity patterns and network activity.

For instance, with LFP and EEG signals, phase detection allows IMD 16 to provide therapy at the correct phase needed to achieve the desired effect. As one example, IMD 16 may induce long-term potentiation if IMD 16 provides electrical stimulation at a peak of the hippocampal theta wave (e.g., when the phase of the hippocampal theta wave is 90°). IMD 16 may induce long term depression, where depression here is meant as the opposite of potentiation, if IMD 16 provides electrical stimulation at a trough of the hippocampal theta wave (e.g., when the phase of the hippocampal theta wave is 270°). Long term potentiation and depression are changes understood to be related to memory storage in neural systems.

Because the phase of the frequency band of the theta wave determines when therapy should be delivered, IMD 16 may be configured for real-time phase detection of the frequency band. However, the techniques described in this disclosure should not be considered as requiring real-time phase detection, and may be usable in various systems in which phase detection of a signal is of interest.

In this disclosure, real-time phase detection refers to determining the instantaneous, current phase of the signal. In other words, very little time may elapse between when IMD 16 determined the phase of the frequency band and the actual phase of the frequency band. As an illustrative example of real-time phase detection, assume that the signal is a sinusoid. In this example, when the amplitude of signal changes from positive to negative, the phase of the signal is 180°. With the real-time phase detection techniques described in this disclosure, no appreciable time elapses between when the amplitude of the signal changes from positive to negative to when IMD 16 determines that the phase of the signal is 180°. Stated yet another way, very little to no portion of the signal, following the time from the point of the signal at which IMD 16 is to determine the phase of the signal, is received by IMD 16 by the time IMD 16 completes determining the phase of the signal.

Real-time phase detection may be beneficial for various purposes. For examples of IMD 16 that sense LFP or EEG signals, real-time phase detection may also improve the ability of IMD 16 to respond to changes in brain state when real-time coupling between other frequency bands serves as an indicator of brain state and the brain state is needed to be known in real-time for the appropriate application of therapy. For example, real-time phase detection may be used in a Phase Amplitude Coupling (PAC) circuit that correlates the amplitude of a gamma waveform to a phase of theta or that correlates the amplitude of a gamma waveform to a phase of beta.

In some cases, using the phase of a frequency band to determine when to deliver therapy may provide for more effective treatment than using other techniques. For example, some techniques may rely on amplitude detection to determine when to deliver therapy or to determine when a subsequent amplitude will occur to determine when therapy is to be delivered. However, the amount of time needed for amplitude detection may be too long to provide therapy at the exact intended amplitude. Also, techniques that rely on amplitude detection to predict the occurrence of when the signal will subsequently be at the intended amplitude are imprecise, which may result in less efficacious treatment.

This disclosure describes example ways in which IMD 16 determines the real-time phase of a frequency band of a signal. Because IMD 16 is implantable, and in some examples, a medical device configured to implement the techniques described in this disclosure may be wearable or otherwise portable, the disclosure describes accurate and computational efficient real-time phase detection. For instance, other techniques for real-time phase detection may require more power than would be advisable for a medical device to deliver and/or may require more circuit space than available on a medical device such as for medical devices that are implantable, wearable, or otherwise portable.

The real-time phase detection techniques may be applied in continuous or discrete time (e.g., on an analog signal or a digital signal). For ease of description, the real-time phase detection techniques are described with respect to a digital signal, in which IMD 16 converts the analog bioelectrical brain signal to a digital bioelectrical brain signal, and implements the techniques on the digital signal. Accordingly, the real-time phase detection techniques are described with respect to digital components such as digital filters. However, the techniques described in this disclosure may be applied to the analog bioelectrical brain signal using analog components such as analog filters.

Moreover, the real-time phase detection techniques may be applied at any frequency and to any frequency band, and applied to all forms of signals, including electrical, mechanical, pressure, and the like. For ease of description, the real-time phase detection techniques are described with respect to different frequency bands of neurological activity in the near or far field, such as for detection the real-time phase of a theta wave in an EEG, where the theta wave includes a frequency band of 4 Hz to 8 Hz of the EEG. However, the techniques can be applied to non-neurological applications, and even non-medical applications such as determining phase of signal outputted by an accelerometer as part of therapy delivery or in examples where the accelerometer is not used for therapy delivery.

As described in more detail below, IMD 16 includes a frequency band phase detector. The frequency band phase detector may be configured for the frequency band of interest (e.g., for the theta wave, as one example). The frequency band phase detector includes one or more frequency component phase detectors, where each frequency component phase detector determines the real-time phase of respective frequency components of the frequency band. The number of frequency component phase detectors may be a function of balancing accuracy, power consumption, and the width of the frequency band.

For example, the frequency band phase detector may include one frequency component phase detector. In this example, the power consumption may be less than examples where the frequency band phase detector includes a plurality of frequency component phase detectors, but the determined phase may be less accurate than examples where the frequency band phase detector includes a plurality of frequency component phase detectors. For purposes of illustration, the disclosure describes examples where the frequency band phase detector includes three frequency component phase detectors (e.g., one for 4 Hz, one for 6 Hz, and one for 8 Hz), but more or fewer frequency component phase detectors if greater or lesser frequency separation may be possible.

Also, for the theta wave, the width of the frequency band is 4 Hz (8 Hz minus 4 Hz). If the frequency band is wider than 4 Hz, then the frequency band phase detector may include more than three frequency component phase detectors. In this example, the frequency separation between each frequency component may be 2 Hz, like in the previous example of one frequency component phase detector for 4 Hz, another for 6 Hz, and a third for 8 Hz, or the frequency separation between each frequency component may be greater than or less than 2 Hz.

Each of the frequency component phase detectors output phase information indicating the phases of respective frequency components. The frequency band phase detector may determine an average (and in some examples, a weighted average) of the phases of each of the respective frequency components. The result of the averaging may be the real-time phase of the frequency band.

To determine the phases of the frequency components, each of the frequency component phase detectors may filter the signal based on the frequency components of respective frequency component phase detectors, wherein the filtering includes correlating the signal with the frequency component for which the frequency component phase detector is configured and by weighing present and more recent portions of the signal at respective frequency components more heavily than earlier portions of the signal as part of the correlation. Also, in some examples, portions of the signal that are received after the instance of when the phase of the frequency band is to be determined may not be used to determine the phase to promote real-time phase detection. In other words, the frequency component phase detectors may determine the phase of respective frequency components without utilizing any portion of the signal that follows in time from the point of the signal at which the phase of the frequency component is determined.

For example, the filtering includes weighing present and more recent portions of the signal at respective frequency components more heavily than earlier portions of the signal by measuring the projection on two elements of a basis set that form phase pairs as determined by performing a correlation operation against those elements. Furthermore, the correlation in the more recent past is weighted more heavily (as it is considered more predictive) than the more distant past in measuring phase. A properly windowed Fourier transform is an example of this technique applied to the basis set pair described by $e^{jwt}$ or $e^{-jwt}$, where $e^{jwt}$ is mathematically equal to $\sin(wt)+j\cos(wt)$ and $e^{-jwt}$ is mathematically equal to $\sin(wt)-j\cos(wt)$.

In general, the filtering may be considered as correlating the signal with the frequency component, by weighing more recent portions of the input signal more heavily than earlier portions of the input signal. When the correlation is based on a sine and cosine waves, the correlation may be considered as a modulation. One way to modulate the signal is by a Fourier transform, in which the signal is modulated by sine and cosine waveforms whose frequency is equal to the frequency of the frequency component for which the frequency component phase detector is configured. In the techniques described in this disclosure, rather than using a symmetric window for the Fourier transform, a non-symmetric window is utilized so that earlier portions of the signal are weighed less than more recent portions of the signal.

The sine wave and cosine wave are examples of a basis set, where a basis set includes waveforms (e.g., mathematical functions) that can be used to form the signal. For example, sine and cosine waves can be used to form the theta wave. However, other examples of basis sets may be used, such as triangular waves as one example. The Fourier transform is used because the derivative of $e^{-jwt}$ is $e^{-jwt}$, and tends to increase computational efficiency and ease of design.

In other words, a Fourier transform measures the projection on a specific element of the basis set described by $\sin wt/\cos wt$ or $e^{+/-jwt}$. The Fourier transform operation is equivalent to performing a correlation operation against $\sin wt$, $\cos wt$ or $e^{-jwt}$ to find the projection onto that element of that basis set. It may be possible to perform such a correlation with any basis set element pair to find the projection (and phase) on these elements of the basis set. As one example, a collection of triangular waveforms that are orthogonal and complete could be used. In this example, orthogonal means an element cannot be formed from other elements and complete means any input signal can be described by a collection of elements. If a theta wave has harmonics, and in some examples a theta wave does have harmonics, it may be possible to use a basis set that is more ideal (e.g., triangular like) and measure the projection onto an element pair to determine the phase. The disclosure uses $e^{-jwt}$ as the basis set because it is the derivative of itself, greatly increasing computational efficiency. Although other basis sets are possible, the disclosure described with respect to the basis set of a Fourier transform.

In a digital application, each of the frequency component phase detectors receives samples of the signal, where the signal is sampled at a sampling frequency. As one example, each of the frequency component phase detectors may determine an estimate of the real-time phase of respective frequency components based on a decreasing weighting of the past samples, and in some examples, a nearly monotonically decreasing weighting of the past samples. The phrase "decreasing weighting" or "decaying weighting" means that the weight assigned to earlier samples is reduced, so that present and more recent samples are weighted more heavily than earlier samples The decreasing weighting of the past samples means a general decreasing weighting of the past samples. It may be possible for there not to be decreased weighting of one or more past samples, but there may be a general trend of decreased weighting. For instance, on average the weighting of past samples is decreasing. In this disclosure, the term "predominantly decreasing" is used to mean that in general the weighting of past samples is decreasing. However, in portions of the disclosure, where the term "predominantly" is not used, it should be assumed that the weighting is generally decreasing (or even always decreasing), and not as a requirement that every previous sample be weighted in decreasing manner.

The weighting of the future sample may be zero for a real-time phase detection algorithm. However, it may be possible to utilize a few future samples to increase accuracy, but with a slight delay in phase detection. For instance, if exact real-time phase detection is not necessary, and a slight delay can be tolerated, then it may be possible to utilize future samples. In the techniques described in this disclosure, future samples are excluded. Also, for analog applications, rather than predominantly decreasing weighting of the past samples of the signal, each of the frequency component phase detectors may decrease the weighting of the past portions of the signal. In this disclosure, the "portion of the signal" is used to generically refer to digital signals or analog signals.

One example way in which each of the frequency component phase detectors may weigh present and more recent samples more heavily than earlier samples of the signal is by a filter that implements a discrete time Fourier transform with exponentially decaying weighting of samples of the signal. The phrase "exponentially decaying" means that the weighting is reducing exponentially. One reason that each of the frequency component phase detectors may utilize a filter that implements a discrete time Fourier transform with exponentially decaying weighting is that such a filter may be implemented with high computational efficiency.

For example, the Fourier transform may be considered as a way to correlate the input signal with the frequency component to which the respective frequency component phase detectors are configured with a basis set that includes sine and cosine waves. With a Fourier transform, the correlation may be considered as a modulation with sine and cosine waves. However, the techniques described in this disclosure are not limited to correlation that uses a Fourier transform, and other correlation using other basis sets may be possible.

Moreover, the techniques described in this disclosure, however, are not limited to example filters that implement a discrete time Fourier transform with exponentially decaying weighting. For example, the frequency component phase detectors may each include a filter that implement exponentially decaying weighting of samples of the signal without using a discrete time Fourier transform. In some examples, the frequency component phase detectors may each include a filter that does not implement exponentially decaying weighting of samples of the signal. Rather, the frequency component phase detectors may each include a filter that implements other types of decaying weighting. As one example, each filter may implement a linear decaying weighting. As another example, each filter may implement a step-wise decaying weighting with multiple steps. Other ways in which decaying weighting may be implemented, and the techniques described above should not be considered limiting. Also, decaying weighting for analog signals, rather than digital samples, may also be possible, and implemented in various ways such as using resistor-capacitor (RC) low pass filters, as one non-limiting example.

With a frequency band phase detector that averages the phase information of phases outputted by one or more frequency component phase detectors that each determine the phase of respective frequency components using a decaying weighting scheme, the frequency band phase detector may be configured to output real-time phase information at a relatively high data rate, and reducing or eliminating latency in knowledge of the real-time phase. In some examples, a minimal amount of current may be needed for such real-time phase detection (e.g., <1 micro-amps) without a drastic increase in circuit space within IMD 16. The frequency band phase detector and its one or more frequency component phase detectors are described in more detail with respect to FIGS. 3 and 5. Prior to describing the frequency band phase detector and the one or more frequency component phase detectors, the following describes the remainder of system 10 in greater detail, and an example of IMD 16 in greater detail.

FIG. 1 illustrates external programmer 14. External programmer 14 is configured to wirelessly communicate with IMD 16 as needed to provide or retrieve therapy information. Programmer 14 is an external computing device that the user (e.g., the clinician and/or patient 12) may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function (i.e., a power button), the buttons and the keypad may be soft keys that change in function depending upon the section of the user interface currently viewed by the user, or any combination thereof. In some examples, the screen (not shown) of programmer 14 may be a touch screen that allows the user to provide input directly to the user interface shown on the display. The user may use a stylus or their finger to provide input to the display.

In some examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to determine a patient state based on activity of a bioelectrical brain signal of patient 12 in one or more frequency bands. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to delivery electrical stimulation therapy to brain of patient 12, but, rather, is only configured to sense one or more physiological parameters of patient 12, including a bioelectrical brain signal of patient 12. This type of IMD 16 may a patient monitoring device useful for diagnosing patient 12, monitoring a patient condition 12, or to train IMD 16 or another IMD for therapy delivery.

Figure 2:
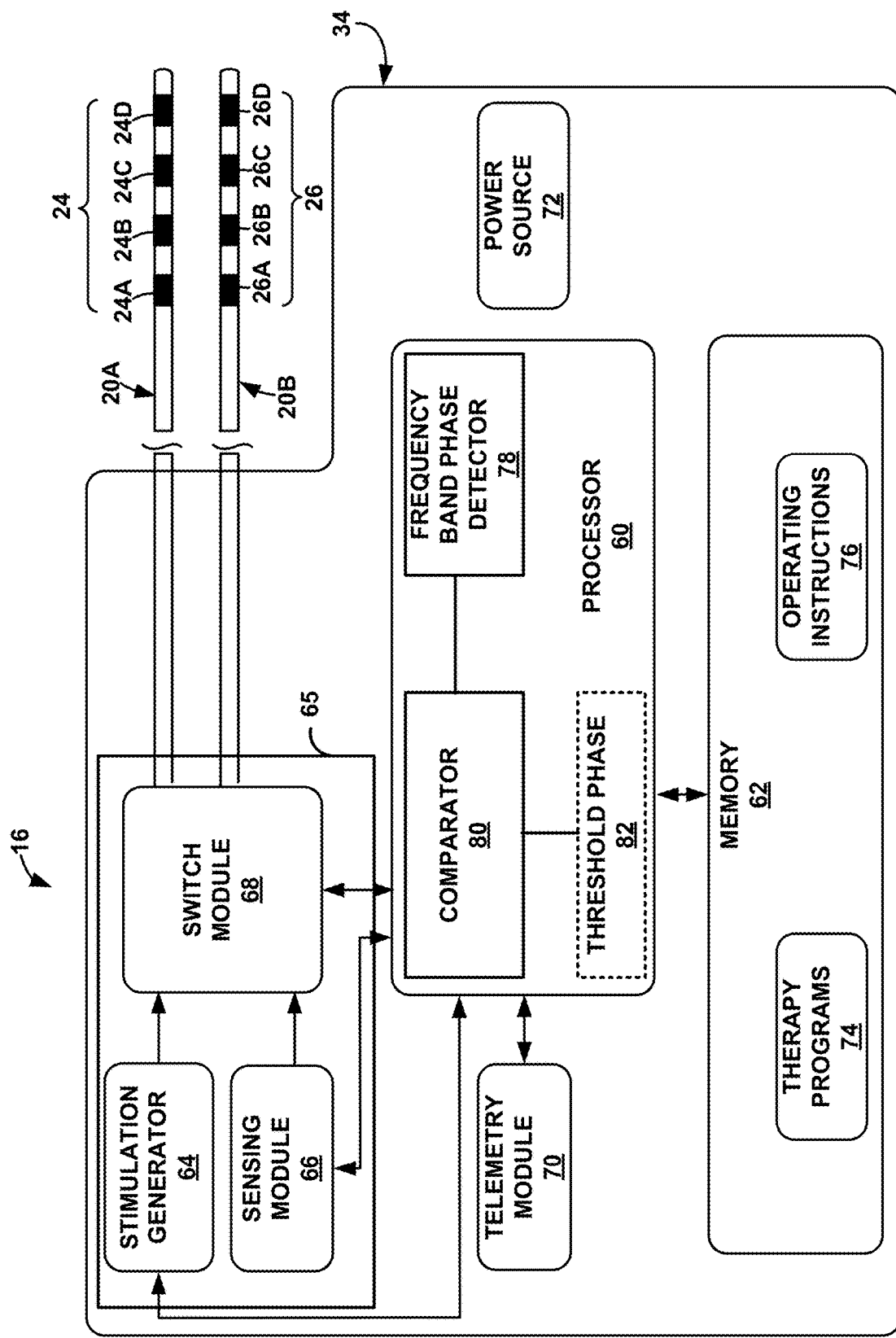
FIG. 2 is functional block diagram illustrating components of an example medical device.

FIG. 2 is functional block diagram illustrating components of an example IMD 16. In the example shown in FIG. 2, IMD 16 includes processor 60, memory 62, therapy module 65, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

Therapy module 65 includes stimulation generator 64, sensing module 66, and switch module 68. Therapy module 65 may be configured to deliver therapy based on the determined phase of the frequency band, where the phase of the frequency band is determined in accordance with the example techniques. For instance, as described in more detail below, stimulation generator 64 may deliver therapy based on a determination by comparator 80 of processor 60. Accordingly, in some examples, processor 60 may instruct therapy module 65 to delivery therapy based on the determined phase of the frequency band.

In the example shown in FIG. 2, memory 62 stores therapy programs 74 and operating instructions 76 (e.g., in separate memories within memory 62 or separate areas within memory 62). Operating instructions 76 may include instructions that cause one or more processors (e.g., processor 60) to implement the example techniques described in this disclosure.

Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. Each stored therapy program 74 may also be referred to as a set of therapy parameter values. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20.

In some examples, however, IMD 16 does not include switch module 68. For instance, rather than switching from a shared source, in some examples of IMD 16, stimulation generator 64 includes individual current or voltage sources for each electrode. These individual current or voltage sources may selectively drive corresponding electrodes.

Stimulation generator 64 may be a single channel or multi-channel stimulation generator. In particular, stimulation generator 64 may be capable of delivering, a single stimulation pulse, multiple stimulation pulses or a continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

As illustrated in FIG. 2, processor 60 includes frequency band phase detector 78 and comparator 80. Frequency band phase detector 78 receives the bioelectrical brain signal from sensing module 66, and determines the phase of a frequency band of the sensed bioelectrical brain signal (e.g., a theta wave) using the example techniques described in this disclosure. In examples where frequency band phase detector 78 operates on digital samples of the signal, sensing module 66 may include an analog-to-digital converter (ADC) that converts the analog brain signal into a digital signal. For instance, the ADC of sensing module 66 may sample the signal at a sampling frequency, referred to as $f_{sr}$, and output the digital samples to frequency band phase detector 78. One example of the sampling frequency is 250 Hz, although other sampling rates are possible, such as at least at the Nyquist rate (e.g., twice the frequency of the brain signal to be analyzed). In examples where frequency band phase detector 78 operates on the analog signal, analog-to-digital conversion may not be necessary, but may be useful for other components of processor 60.

Frequency band phase detector 78 outputs phase information indicative of the determined phase to comparator 80. Comparator 80 also receives a threshold phase 82. In some examples, comparator 80 determines whether the determined phase equals threshold phase 82. In response to a determination that the determined phase equals threshold phase 82, processor 60 causes stimulation generator 64 to output stimulation via leads 20A, 20B.

Threshold phase 82 is illustrated in a dashed box to indicate that threshold phase 82 is a stored phase value used for comparison purposes. In FIG. 2, a register of processor 60 may store threshold phase 82. However, it may be possible for memory 62 to store threshold phase 82.

The value of threshold phase 82 may be user selected during testing or may be preset. For instance, as described above, to induce long-term potentiation, IMD 16 may output electrical stimulation at a peak of a hippocampal theta wave. For this example, the value of threshold phase 82 may be 90°, and when frequency band phase detector 78 determines, in real-time, that the phase of the theta wave is 90°, comparator 80, under control of processor 60, may cause stimulation generator 64 to output stimulation. As another example, as described above, to induce long-term depression (e.g., the opposite of potentiation in this context), IMD 16 may output electrical stimulation at a trough of a hippocampal theta wave. For this example, the value of threshold phase 82 may be 270°, and when frequency band phase detector 78 determines, in real-time, that the phase of the theta wave is 270°, comparator 80, under control of processor 60, may cause stimulation generator 64 to output stimulation.

It should be understood that frequency band phase detector 78 and/or comparator 80 being part of processor 60 is provided for purposes of illustration only and should not be considered limiting. In some examples, frequency band phase detector 78 and/or comparator 80 may be external to processor 60, and be their own, independent components. In some examples, frequency band phase detector 78 may be software or firmware executing on processor 60, may be hardware components, or a combination of both software or firmware and hardware.

Also, the above example where comparator 80 causes stimulation generator 64 to output stimulation when the phase, as determined by frequency band phase detector 78, equals threshold phase 82 is merely one example and should not be considered limiting. The phase, as determined by frequency band phase detector 78, may be useful for other purposes as well, such as diagnosis purposes. In general, IMD 16 or programmer 14, or possibly some other device in a medical system may take some action based on the determined phase of the frequency band.

For instance, frequency band phase detector 78 may determine the phase, and processor 60 may utilize this information to estimate the timing of when peaks or valleys in the signal are to occur. If processor 60 determines that peaks or valleys in the signal did not occur at the estimated time, processor 60 may indicate as such, and external programmer 14 or the clinician may utilize the information for diagnosing the patient. There may be various other purposes of phase detection, and the example described with respect to FIG. 2 is merely one of the purposes.

Inclusion of frequency band phase detector 78 in processor 60 or, more generally, in IMD 16, may have minimal effect on the power consumption and circuit space. For example, frequency band phase detector 78 may consume a maximum of 1 micro-amp. Also, frequency band phase detector 78 may be implemented in a computational efficient manner, meaning that additional components in processor 60 to handle complex tasks may not be needed.

In some examples, in addition to outputting the phase of the frequency band to comparator 80, frequency band phase detector 78, via processor 60, may output the phase value of the frequency band, via telemetry module 70, to programmer 14 for presentation. For instance, processor 60 may output the sensed signal and the determined phase of the frequency band as the signal is being sensed (e.g., output the sensed signal and the determined phase of the frequency band in real-time). In some examples, at least for the phase information being outputted to program 14, processor 60 may add a fixed and known phase shift to the real-time phase information determined by frequency band phase detector 78. The purpose of the phase shift may be to align the π to −π transition along an application-specific key phase point (e.g., trough or peak of an EEG theta wave), which may aid in visual analysis.

Figure 3:
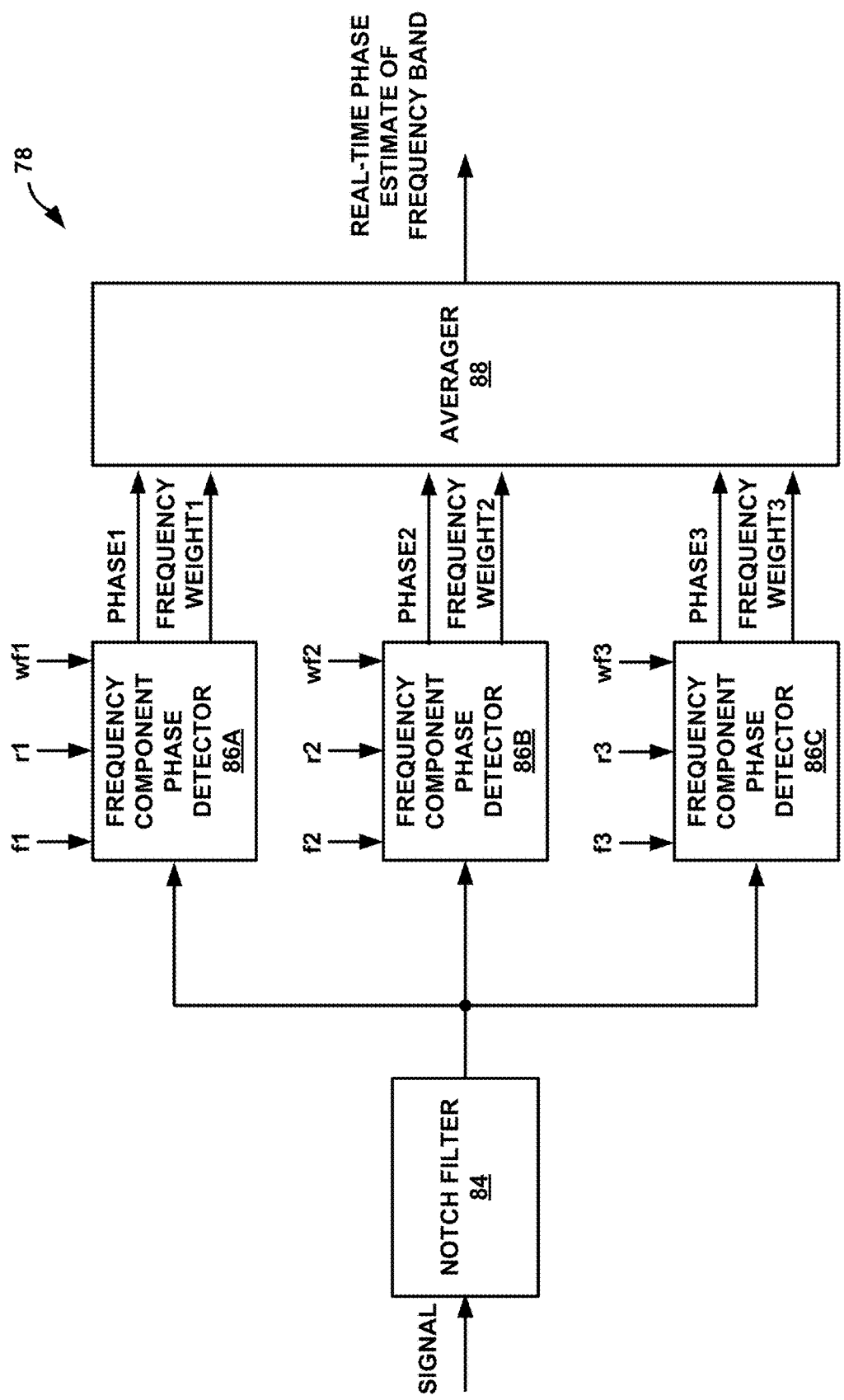
FIG. 3 is a block diagram illustrating components of an example frequency band phase detector.

FIG. 3 is a block diagram illustrating components of an example frequency band phase detector. For instance, FIG. 3 illustrates frequency band phase detector 78 in greater detail. As illustrated, frequency band phase detector 78 includes notch filter 84, frequency component phase detectors 86A-86C, and average 88. In the example of FIG. 3, frequency band phase detector 78 receives a digital signal (e.g., an analog-to-digital converted signal), where one example of the digital signal is an EEG waveform that is sampled at a sampling rate of 250 Hz.

As illustrated, notch filter 84 of frequency band phase detector 78 receives the signal (e.g., from sensing module 66). Notch filter 84 is an optional filter and may not be needed in every example. Notch filter 84 may be configured to filter out frequencies that contribute noise to the overall signal. For instance, as described in more detail, frequency component phase detectors 86A-86C may function as a bandpass filter, and notch filter 84 may function as a pre-filter to filter out noise from the signal before being bandpass filtered by frequency component phase detectors 86A-86C.

As an example, in a bioelectrical brain signal, there may be a lot of noise in the area centered at 0 Hz. Notch filter 84 may filter out the 0 Hz component from the signal. In one example, the equation of notch filter 84 is:

$(1-z^{-1})(1+z^{-1})/(1-r_2 z^{-1})$, where $r_2$ equals 0.90, the notch is at 0 Hz, and a zero at −1.

There may be other ways in which to pre-filter the signal (e.g., filter prior to frequency component phase detectors receiving the signal), and notch filter 84 should not be considered limiting. Also, in the above example, there is noise at 0 Hz. However, in other examples, where a different frequency includes particularly noisy signal components, notch filter 84 may be configured to filter out such frequencies. If there are not frequencies for which there is a lot of noise, notch filter 84 may not be needed.

In general, notch filter 84 may be considered as applying pre-filtering prior to the phase detection. While it is possible for notch filter 84 to add some phase delay, thereby reducing the accuracy of the phase detection, the effect of the phase delay may be relatively small (e.g., negligibly small), and in any case, can be accounted for in the phase calculation.

For example, the phase delay as a function of frequency can be calculated for any pre-filter (e.g., for notch filter 84, in this example). As described in more detail, each one of frequency component phase detectors 86A-86C may be configured to determine the phase for respective frequency components. Also, the phase delay for each of the frequency components may be different through notch filter 84. Accordingly, for each of frequency component phase detectors 86A-86C, a known phase delay, which corresponds to the frequency component for which they are configured, resulting from notch filter 84, can be added to account for the delay through notch filter 84. In one example, averager 88 may account for the delay through notch filter 84. In one example, frequency component phase detectors 86A-86C may account for the delay through notch filter 84. There may be other ways in which to account for the delay through notch filter 84, and the techniques are not limited to the above examples.

For bioelectrical brain signals, where the EEG theta band is of interest, the non-theta frequency content resembles 1/f noise. Accordingly, to eliminate the large noise content around 0 Hz, notch filter 84 is applied at 0 Hz. The high frequency noise is lessened by adding a zero at −1 on the unit circle. Again, notch filter 84 may be optional, or may be reconfigured to apply a notch at another frequency if the frequency bands not of interest (e.g., non-theta frequencies) resemble different content than 1/f noise.

As illustrated, frequency band phase detector includes three frequency component phase detectors 86A-8C. In some examples, there may be more or fewer frequency component phase detectors. Each of frequency component phase detectors 86A-86C receives the output from notch filter 84. Each one of frequency component phase detectors 86A-86C may be substantially the same, and can be configured for respective frequency components.

As illustrated, each one of frequency component phase detectors 86A-86C receives three variables: f, r, and weight factor (wf), where f1, r1, and wf1 are for frequency component phase detector 86A, f2, r2, and wf2 are for frequency component phase detector 86B, and f3, r3, and wf3 are for frequency component phase detector 86C. In some examples, rather than receiving these variables, each one of frequency component phase detectors 86A-86C may be pre-configured with set values for one or more of f, r, or wf. To allow frequency component phase detectors 86A-86C to be basic building blocks, in some examples, frequency component phase detectors 86A-86C may receive the values for one or more of variables f, r, or wf so that frequency component phase detectors 86A-86C are configurable for the intended frequency band.

The variable "f" refers to the frequency component of the frequency band for which each one frequency component phase detectors 86A-86C are to determine the phase. For example, for a theta wave with frequency band of 4 Hz to 8 Hz, f1 may equal 4 Hz, f2 may equal 6 Hz, and f3 may equal 8 Hz. In this example, frequency component phase detector 86A is configured to determine the phase for the 4 Hz frequency component of the signal, frequency component phase detector 86B is configured to determine the phase for the 6 Hz frequency component of the signal, and frequency component phase detector 86C is configured to determine the phase for the 8 Hz frequency component of the signal.

The variable "r" sets the rate of decay of the weighting of earlier samples. As described in more detail, the variable "r" sets a pole at the decaying weighted filter described in FIG. 5. For example, the multiplicative factor that any previous sample is reduced on the next cycle is "r." As one example, if "r" equals 0.97, then the weighting of the every previous point used in the last calculation will be 0.97 times what it was in the past. In effect, the larger the value of "r," the bigger the time constant, the poorer the time resolution, and the better the frequency resolution. The smaller the "r," the smaller the time constant, the better the time resolution, and the poorer the frequency resolution. The value of "r" may be configurable based on the trade-off between time and frequency resolution.

In the examples described in this disclosure, the value of "r" is less than one. As one example, the value of r is 0.97 for each of r1, r2, and r3. The values r1, r2, and r3 may be the same values, in some examples, or different values, in some examples. In some examples, the value of r may be greater than 0.8, and less than one, but the techniques should not be considered limiting in this way.

The "wf" variable is used to determine the weight factor that is applied to the phase information determined by each of frequency component phase detectors 86A-86C for respective phases. For instance, conceptually, the decaying weighting of earlier samples results in each of frequency component phase detectors 86A-86C functioning as a resonator (e.g., leaky resonator) around the frequency component defined by the variable "f." For example, as illustrated and described in more detail with respect to FIG. 5, each one of frequency component phase detectors 86A-86C utilizes a weighting filter (e.g., decaying weighted filter 90 of FIG. 5 described below) to implement the decaying weighting of earlier samples.

In the frequency domain, the transfer function of the weighting filter of each of frequency component phase detectors 86A-86C appears like a Gaussian curve. In the example illustrated in FIG. 3, the combination of three frequency component phase detectors 86A-86C can be considered as a summation of three Gaussian curves each centered around respective frequency components of 4 Hz, 6 Hz, and 8 Hz. The summation of three Gaussian-like curves each centered around respective frequency components of 4 Hz, 6 Hz, and 8 Hz results in a bandpass filter transfer function with a band of 4 Hz to 8 Hz.

The variable "wf" is used to control the contribution of the Gaussian-like curves for each of the frequency components. For example, for the Gaussian-like curve of the 4 Hz component, the contribution of frequencies greater than 4 Hz sum with the Gaussian-like curve of the 6 Hz component and sum with the contribution of frequencies less than 8 Hz for the Gaussian-like curve of the 8 Hz, resulting in a peak in the 6 Hz component. The variable "wf" is used to control such peaking.

In other words, for proper phase detection, it may be desirable for the weighting filters of each of frequency component phase detectors 86A-86C to add together to form a bandpass filter with unity gain (e.g., same gain across 4 Hz to 8 Hz, with reduction in amplitude for signals less than 4 Hz and reduction in amplitude for signals greater than 8 Hz). However, without band weighting, the leaky resonator behavior is additive, and there is not unity gain across the band. By selecting the appropriate values for wf1, wf2, and wf3, it is possible to control the contribution of each of the leaky resonators so that there is nearly unity gain across the frequency band.

With the appropriate values for wf1, wf2, and wf3, each one of frequency component phase detectors 86A-86C may determine respective frequency weights, identified as FREQUENCY WEIGHTS1-3 in FIG. 3. The "frequency weights" and the "weighting of samples" (e.g., decaying weighting) should not be confused. The frequency weights define the amount that each of the frequency components contributed to the final determination of the phase of the frequency band. The weighting of samples refers to the amount that each sample contributes to the determination of a phase of the frequency component.

As illustrated, each one of frequency component phase detectors 86A-86C output phase information, identified as PHASE 1-3 in FIG. 3, of phases of respective frequency components, and respective frequency weights. Averager 88 receives the phase information for respective frequency components and frequency weights. Averager 88 may determine a weighted average to determine the phase of the frequency band. For instance, average 88 may implement the following equation:

Phase of Frequency Band=((phase1)(frequency weight1)+(phase2)(frequency weight2)+(phase3) (frequency weight3))/(frequency weight1+frequency weight2+frequency weight3).

The above equation may be implemented by averager 88 to determine the phase of the frequency band in one example. There may be other ways in which averager 88 may determine the phase of the frequency band. For instance, each of the frequency weights outputted by respective frequency component phase detectors 86A-86C may be considered as an amplitude. In this example, each corresponding frequency weight and phase may define a phasor, where the frequency weight is the amplitude and the phase is the angle of the phasor (e.g., frequency weight1 and phase1 together define phasor1, frequency weight2 and phase2 together define phasor2, and frequency weight3 and phase3 together define phasor3).

In some examples, averager 88 may perform a vector sum of the phasors and determine the angle of the total summation vector to determine the phase of the frequency band.

Phase of Frequency Band=angle($\Sigma^n_{k=1} A_k$(cos $\theta_k$+i sin $\theta_k$)).

In the above equation, $A_k$ is the frequency weight outputted by respective frequency component phase detectors 86A-86C (e.g., frequency weight1-frequency weight3). Also, $\theta_k$ equals the phase outputs from respective frequency component phase detectors 86A-86C (e.g., phase1-phase3).

The techniques for determining the phase of frequency band based on phasors may be considered as using the vector sum of the output phasors from three frequency component phase detectors with different resonant frequencies to estimate the real-time phase of a frequency band within the incoming EEG waveform. These techniques for determining the phase of the frequency based on phasors may be considered as a generalization of the equation for the simple weighted average of phase described above. For instance, in the absence of noise, when vectors share nearly the same angle, the small angle approximation can be applied, reducing the equation of Phase of Frequency Band=angle($\Sigma^n_{k=1} A_k$ (cos $\theta_k$+i sin $\theta_k$)) to Phase of Frequency Band=((phase1) (frequency weight1)+(phase2)(frequency weight2)+ (phase3)(frequency weight3))/(frequency weight1+ frequency weight2+frequency weight3).

This generalization is useful as it allows an arbitrary filter to be constructed that is applicable to any given frequency phase of a LPF or EEG band oscillator, such as the theta rhythm. This is because an LFP oscillation can vary within a larger frequency range that cannot be adequately tracked using only one of frequency component phase detectors 86A-86C; for example, the so-called "theta band" has about a 4 Hz wide variation in frequency ranging, in some cases, from 4 Hz to 8 Hz. Without the constructed, idealized band, when the input frequency moves away from peak resonance of a single resonator, the recent past is weighted less heavily than the more distance past, resulting in a sluggish phase-change response. Furthermore, given that different subjects, brain states, or brain regions can exhibit differences in theta band frequency characteristics, one advantage of this method is that the band pass shape can be optimized for patients and signal origin by simple parametric adjustment.

It should be understood that a weighted average is not necessary in every example. In such examples, the variable "wf" or the determination of the frequency weights may also not be necessary.

In some examples, averager 88 may be configured with phase delay information of notch filter 84 for each of the respective frequency components. It should be understood that even in examples where there is no notch filter 84, there may be some other components that add phase delay, and averager 88 may be configured with such phase delay information for each of the respective frequency components. Averager 88 may add (or subtract) the phase delay information for respective frequency components with respective ones of PHASE1-3. Averager 88 may utilize the resulting respective values in the above equation, rather than PHASE1-3, to determine the phase of the frequency band.

Figure 4A:
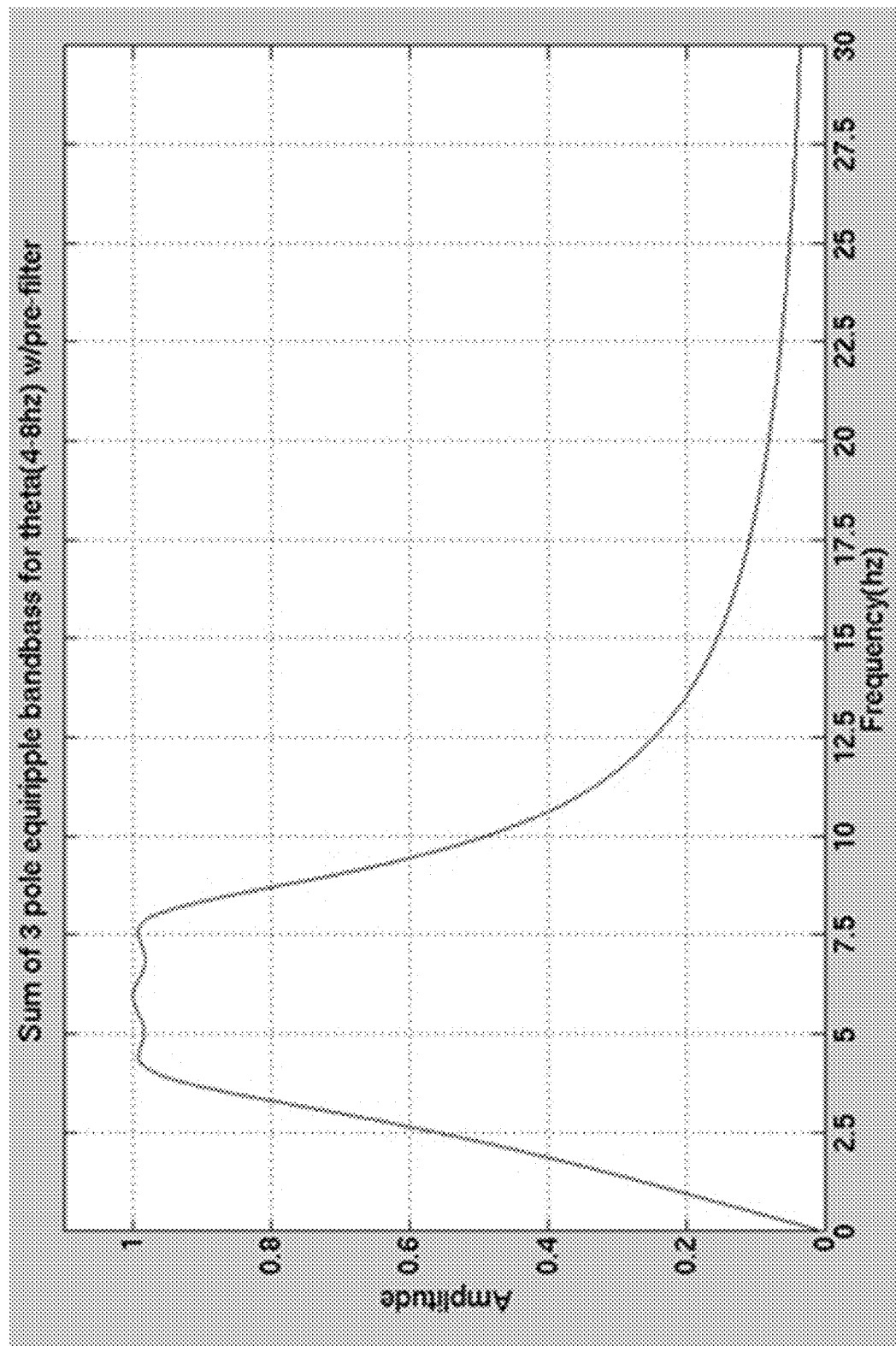
FIG. 4A is a graph illustrating a constructed band with pre-filter for a collection of theta waves.

FIG. 4A is a graphical diagram illustrating a constructed band with pre-filter for a collection of theta waves. In other words, FIG. 4A illustrates an example bandpass structure for phase estimation of EEG theta wave. The bandpass structure may be, in some cases, optimal for a collection of EEG theta waves. As described above, each one of frequency component phase detectors 86A-86C may be considered as resonators for selecting their respective frequency components, and provide a Gaussian like roll off.

As illustrated in FIG. 4A, for frequencies above 8 Hz, the roll off appears Gaussian, and is the result of the summation of the roll off from each of frequency component phase detectors 86A-86C for respective frequency components of 4 Hz, 6 Hz, and 8 Hz. The roll off, for frequencies less than 4 Hz, does not appear Gaussian because of notch filter 84.

Also, as illustrated in FIG. 4A, over the 4 Hz to 8 Hz band, the gain is approximately unity, with the three ripple peaks corresponding to the respective frequency components of 4 Hz, 6 Hz, and 8 Hz. In some examples, the amplitude of the ripple peaks may be controlled by the "wf" variable described above.

Figure 4B:
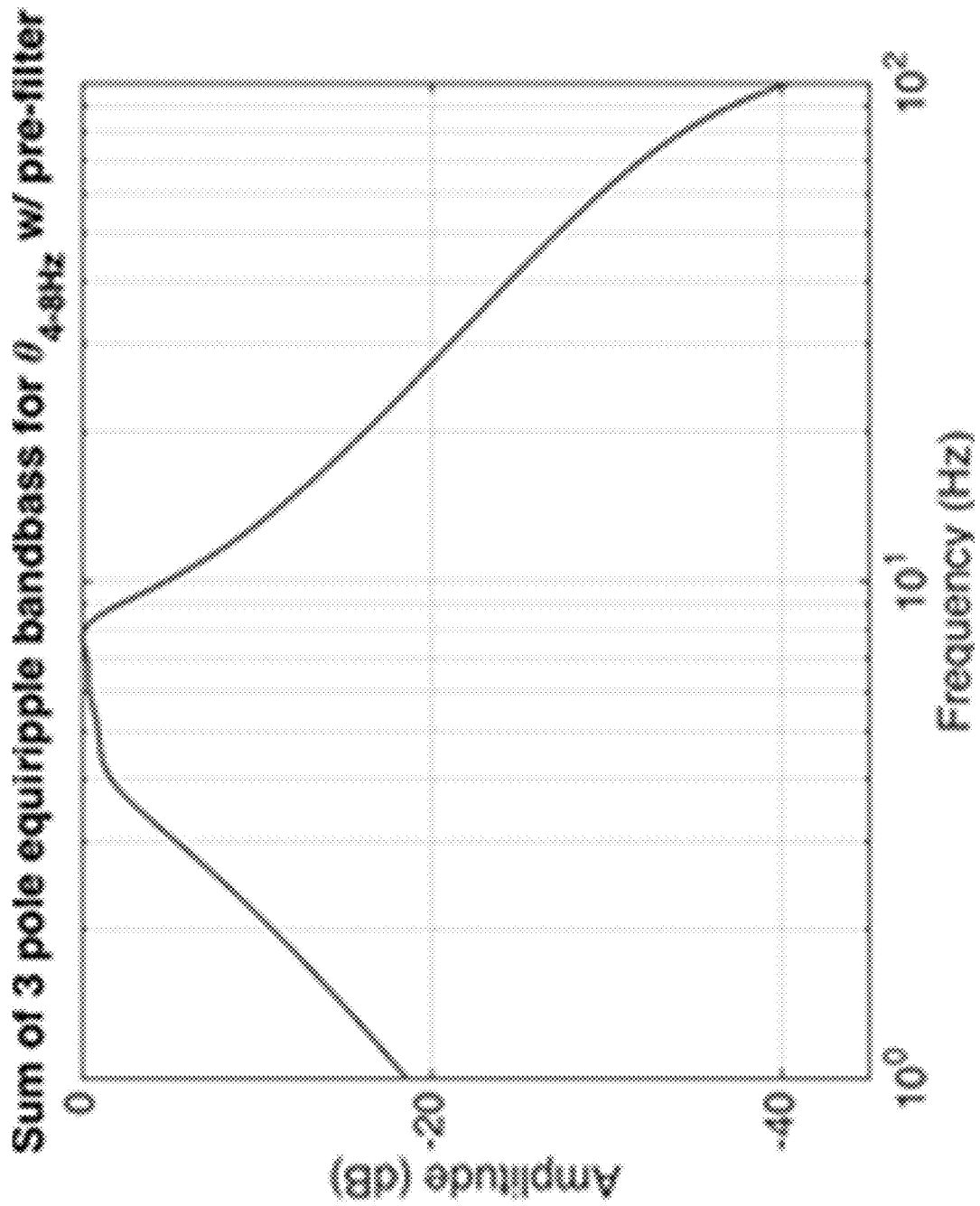
FIG. 4B is a graph illustrating another constructed band with pre-filter for a collection of theta waves.

FIG. 4B is another graphical diagram illustrating a constructed band with pre-filter for a collection of theta waves. FIG. 4B is similar to FIG. 4A expect that FIG. 4B is illustrated on a log-scale and FIG. 4A is illustrated on a linear-scale. Also, the weighting of each one of frequency component phase detectors 86A-86C (e.g., the "wf" variable for each of frequency component phase detectors 86A-86C) may be different in FIGS. 4A and 4B. In FIG. 4B, the weighting for 4 Hz, 6 Hz, and 8 Hz resonators (e.g., frequency component phase detectors 86A, 86B, and 86C, respectively) is 1.98, 1.00, and 1.70, respectively.

The example illustrated in FIG. 4B may function better for 1/f noise of the brain because the band pass amplitude is less at 4 Hz than 8 Hz. The example illustrated in FIG. 4A may perform better in a white noise environment. In general, there may not be much difference in the performance between the examples illustrated in FIGS. 4A and 4B, and the example illustrated in FIG. 4B is directed more towards the specific example of measuring the phase of the theta wave in the brain which has more 1/f noise than general white noise. In other words, the techniques described in this disclosure may be optimized for the specific noise characterized for the system in which the techniques are being implemented (e.g., optimized to reduce the 1/f noise in the brain or optimized if there is white noise for another system, either in the brain or otherwise).

Figure 5:
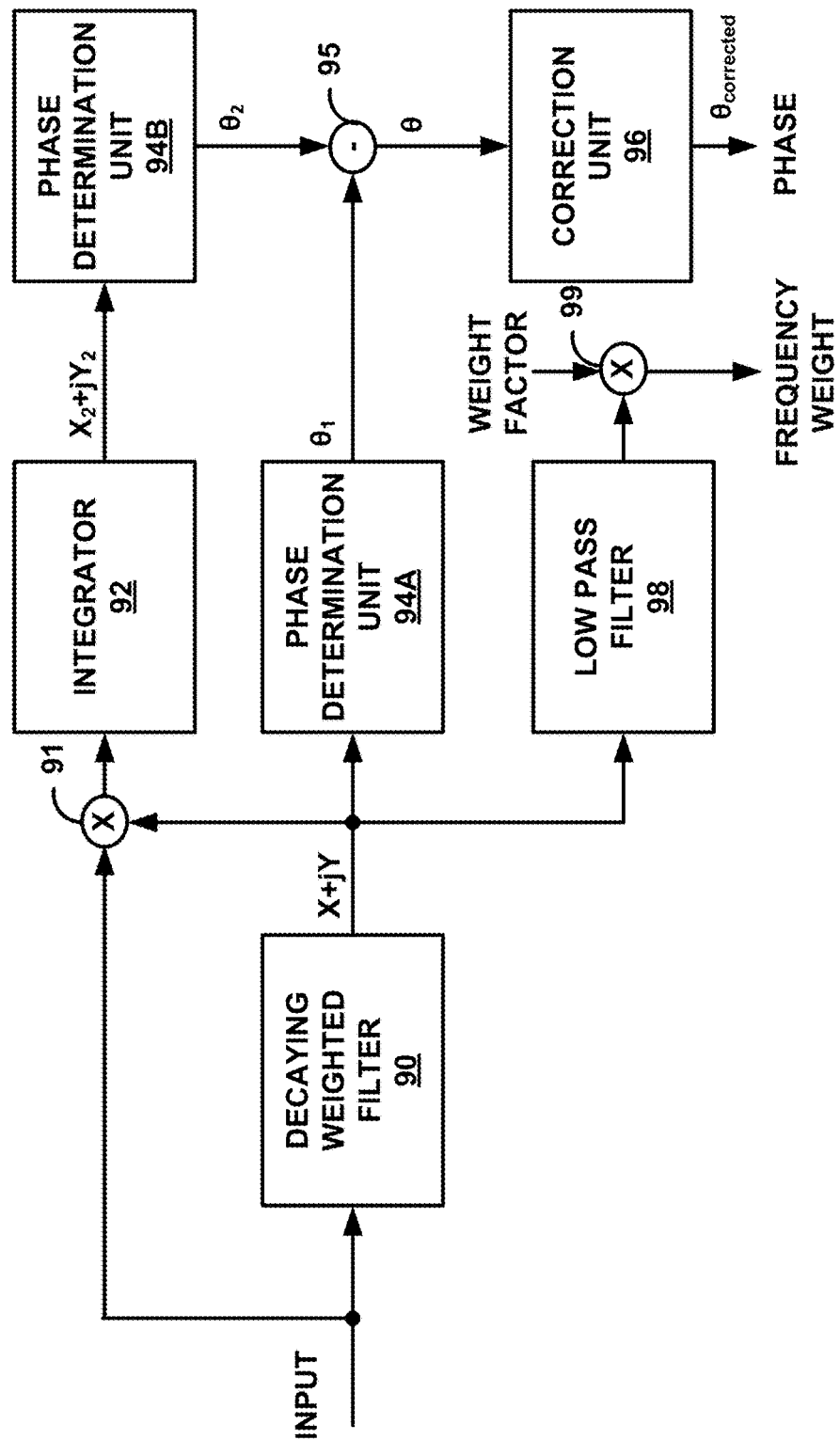
FIG. 5 is a block diagram illustrating an example of a frequency component phase detector.

FIG. 5 is a block diagram illustrating an example of a frequency component phase detector. FIG. 5 illustrates a generic example of frequency component phase detector 86. For instance, frequency component phase detectors 86A-86C may be substantially the same as frequency component phase detector 86 illustrated in FIG. 5. Frequency component phase detector 86 may be considered as a real-time Fourier transform (RTFT) block, and may be a leaky resonator-based RTFT implementation that is computationally efficient.

As illustrated, decaying weighted filter 90 receives an input signal. In some examples, the input signal may be the output of notch filter 84, and in some examples, may be the sampled signal (e.g., sampled bioelectrical brain signal). In either example, the input signal may be digital signal that has been sampled at a sampling rate of $f_{sr}$ (e.g., 250 Hz). In analog implementation, the input signal to decaying weighted filter 90 may be the analog signal (or an analog filtered version of the analog signal). For ease of description, the example illustrated in FIG. 5 is described with respect to a digital implementation, but the techniques may be extended to analog implementations as well.

Decaying weighted filter 90 may implement the following transfer function to filter the input signal in such a way that present and more recent samples of the input signal are weighted more heavily in determining the phase of the frequency component than earlier samples of the input signal. The transfer function of decaying weighted filter 90 may be:

$$H(z) = 1/(1 - re^{+jw}z^{-1}) \quad \text{(equation 1)}.$$

In equation 1, "r" equals the decaying weighting factor that determines the rate of decay of the weighting applied to the previous samples as described above, and "w" equals $2*\pi*(f/f_{sr})$, where "f" equals the frequency component as described above.

In general, the transfer function of decaying weighted filter 90 may be considered as correlation equation in which the input signal is correlated with the frequency of the frequency component for which frequency component phase detector is configured, in which more recent samples of the signal are weighted more heavily than earlier portions of the signal. The transfer function of decaying weighted filter 90 (e.g., H(z)) may be utilized because it provides for an exponentially decaying weighting of earlier samples, as described in more detail below, and generally because such a transfer function can be implemented as a digital filter in an computationally efficient manner. However, the transfer function in equation 1 should not be considered limiting. In some examples, other transfer functions in which earlier samples of the input signal are weighed less than present and more recent samples of the input signal are possible, such as transfer functions that implement a linearly decaying weighting, a step-wise decaying weighting, or other possible decaying weighting techniques.

One example way in which to implement an exponentially decaying weighting function is with a discrete time Fourier transform with exponentially decaying weighting. The Fourier transform may be considered as a correlation with a basis set that includes sine and cosine waves with a frequency equal to the frequency of the frequency component for which frequency component phase detector 86 is configured, and may be referred to as modulating the input signal. However, a basis set of sine and cosine waves is not necessary, and decaying weighted filter 90 may correlate the input signal with a frequency equal to the frequency component for which frequency component phase detector 86 is configured with a basis set different than sine and cosine waves (e.g., triangular waves). In these examples, the weighting of present and recent samples may be more heavy than earlier samples as part of the correlation calculation (e.g., predominantly decreasing weighting of portions of the signal).

The equation for the discrete time Fourier transform with exponentially decaying weighting is:

$$X(w) = \sum_{n=-\inf}^{0} r^{-n} e^{-jwn} x(n). \quad \text{(equation 2)}$$

In equation 2, x(n) represents the samples of the signal. The variables "r" and "w" are the same as above with respect to equation 1, where "r" is less than one. The weighting function of equation 2 may function well for its ideal predictive properties and computationally efficient implementation.

Mathematically, equation 2 can be rewritten as a geometric series, which is the same as equation 1 (i.e., $H(z) = 1/(1 - re^{+jw}z^{-1})$). In this way, decaying weighted filter 90 implements a weighted Fourier transform at w equals $2*\pi*f/f_{sr}$ to weigh earlier samples of the signal less heavily than present and more recent samples of the signal.

Multiplying the numerator and denominator of equation 2 by the complex conjugate of the denominator yields:

$$H(z) = (1 - re^{-jw}z^{-1})/(1 - 2r\cos(w)z^{-1} + r^2 z^{-2}) \quad \text{(equation 3)}.$$

The denominator of equation 3 is the transfer function of a leaky resonator formed by poles located at radius "r" and angle "w" and "−w" on the unit circle. The numerator of equation 3 converts the output of the leaky resonator to a complex frequency component. For this reason, frequency component phase detector 86 may be considered as a leaky resonator building block, where one or more leaky resonator building blocks (e.g., frequency component phase detectors 86A-86C) together are used to determine the real-time phase of the frequency band, as illustrated in FIG. 3 and described above with respect to FIG. 3.

In the example illustrated in FIG. 5, equations 1-3 may be considered as correlating the input signal with frequency component based on a predominantly decreasing weighting of the input signal. For instance, with a Fourier transform the correlation may be considered as modulation in which the input signal is modulated by cos((frequency component)*t)+/−j sin((frequency component)*t). However, with a weighted Fourier transform (e.g., decaying weighting), earlier portions of the input signal are weighed less than more recent portions. In this example, the cosine and sine waves are examples of a basis set, but there may be other possible basis sets. As described above, a basis set includes mathematical functions that can be used to represent a signal of interest (e.g., sine and cosine waves can be used to represent a theta wave, but other possible waves may also be used to represent the theta wave, such as triangular waveforms).

As illustrated in FIG. 5, the output of decaying weighted filter 90 is referred to as a filtered signal, and is a complex phasor: X+jY. The amplitude of the output of decaying weighted filter 90 (e.g., the amplitude of the filtered signal) is based on the magnitude of X+jY (i.e., sqrt($X^2+Y^2$)). The phase of the output of decaying weighted filter 90 (e.g., the filtered signal) is given by the angle of X+jY (i.e., arctangent of Y/X). For example, phase determination unit 94A receives the output from decaying weighted filter 90, and determines the phase of the filtered signal outputted by decaying weighted filter 90 by determining (a tan(Y/X). The determined phase of the output of decaying weighted filter 90, as determined by phase determination unit 94A is referred to as $\theta_1$.

In FIG. 5, $\theta_1$ represents the phase of the frequency component at the input of the filter plus any phase delay added by decaying weighted filter 90. This phase delay added by decaying weighted filter 90 is referred to as an unaccounted for phase delay or, more simply, as a phase error. In this disclosure, the determined phase of the filtered signal includes the phase of the frequency component and a phase error. In other words, $\theta_1$ is a noisy estimate of the phase of the frequency component because it includes the actual phase of the frequency component and a phase error.

In general, the unaccounted for phase delay represents the phase delay added by decaying weighted filter 90, where the amount of phase delay decaying weighted filter 90 adds to each frequency of the input signal may be different. For instance, in a discrete time Fourier transform without exponentially decaying weighting, the phases of all frequency components of the signal change by the exact same amount. However, although decaying weighted filter 90 attenuates frequencies other than the frequency for which frequency component phase detector 86 is configured, these other frequencies are not completely removed, and the amount by which the phase changes, for some of these other frequencies, varies. In other words, the phase delay added by decaying weighted filter 90 is not the same for each of the frequency components of the input signal.

Frequency component phase detector 86 may be configured to implement a self-correlation (or self-modulation) technique to measure the unaccounted for phase delay and subtract the unaccounted for phase delay from the phase determined by phase determination unit 94A to determine an initial estimate of the phase of the frequency component. For example, frequency component phase detector 86 may determine the unaccounted for phase error and phase delay in the filtered signal outputted by decaying weighted filter 90 by comparing it with the input signal, where such comparison is performed by correlating (in some examples, modulating where sine and cosine waves are used) the input signal with the complex frequency component phasor at the output of the weighted Fourier transform performed by decaying weighted filter 90 (e.g., the filtered output signal represented by X+jY). In other words, frequency component phase detector 86 may determine a phase of the filtered signal, determine the phase error, and subtract the determined phase error from the phase of the filtered signal to determine an initial phase of the frequency component.

For example, correlation unit 91 may correlate the input, received signal with the filtered signal (represented, in FIG. 5, by the complex output phasor X+jY) outputted by decaying weighted filter 90. In this manner, correlation unit 91 may correlate the input signal to the baseband with the unaccounted for phase delay resulting from decaying weighted filter 90 given by the angle of the complex baseband.

Integrator 92, also referred to as a leaky integrator, receives the output of correlation unit 91, and low pass filters the signal to remove high frequency content (e.g., isolating the output of correlation unit 91 from high frequency content). For example, integrator 92 may filter a signal resulting from the correlation to generate a filtered correlated signal. Integrator 92 may implement the following transfer function to filter the output of modulation unit 91:

$$H_{int}(z)=1/(1-rz^{-1})$$ (equation 4).

In equation 4, integrator 92 uses the same temporal weighting as equation 1. In other words, the variable "r" in equation 4 is the same as the variable "r" in equation 1.

As illustrated in FIG. 5, the output of integrator 92 (e.g., the filtered correlation signal) is represented by the phasor: $X_2+jY_2$. Phase determination unit 94B may determine the phase of the filtered correlated signal (e.g., the output of integrator 92) by determining the arc-tangent of $Y_2/X_2$. For example, the unaccounted for phase error phase delay (e.g., phase error) is determined by the angle of a low frequency pass version of the complex signal resulting from the modulation. The output of phase determination unit 94B is the unaccounted for phase delay (e.g., phase error), referred to as $\theta_2$. Subtraction unit 95 may subtract the output of phase determination unit 94B from the output of phase determination unit 94A (e.g., $\theta_1-\theta_2$), referred to as $\theta$. In this example, $\theta$ is an initial estimate phase of the frequency component.

In the example of FIG. 5, frequency changes and corresponding phase shifts on the input signal, not yet reflected in the output of equation 1, are directly fed into the phase measurement performed by the modulation and equation 4, correcting for this shift as part of the phase delay measurement. In this example, the exponential decay in the weighting of past information is maintained in estimating the phase, even with the inclusion of integrator 92.

In this sense, although the disclosure focuses on real-time phase estimation of sinusoids the concept is extensible to other periodic basis sets as well, perhaps more representative of the underlying signal, like triangular waveforms. In this disclosure, a weighted Fourier transform is replaced by two (or more) correlation operations against phase shifted basis elements where the relative amplitudes resulting from the correlation operations are used to determine the noisy estimate of phase (e.g., phase of the filtered output signal that decaying weighting filter 90 outputs). The non-linear phase delay resulting from the asymmetric correlation window of decaying weighting filter 90 is corrected for by performing a correlation by correlation unit 91 of the generalized phasor (e.g., X+jY) resulting from this noisy estimate (e.g., phase of the filtered output signal from decaying weighting filter 90) against the input signal. It should be noted that without the convenient properties of a sinusoidal basis set this more general approach may be more accurate, but may not be as computationally efficient.

In some examples, the output of decaying weighted filter 90 may include high frequency components that result from decaying weighted filter 90 applying a discrete time Fourier transform. For example, the techniques described in this disclosure may function well when the decay of the window of the Fourier transform is significant compared to the period of the frequency band (e.g., as described below, in some examples a factor Q is needed, which is based on the decay variable "r" and the frequency of the input signal and the frequency component). However, a Fourier transform modulates the desired frequency (e.g., the frequency component to which frequency component phase detector 86 is configured) to baseband with $e^{-jw}$ equals cos(wn)−j*sin (wn), but also creates an up-modulated signal content at twice the modulation frequency. The low-pass filtering capabilities of decaying weighted filter 90 (e.g., via the decaying window function) will reduce the amplitude of the high frequency up-modulated signal; however, such low-pass filtering does not remove the high frequency up-modulated signal completely.

For instance, assume that frequency component phase detector 86 is configured for the 6 Hz frequency component. In this example, decaying weighted filter 90 may produce content at 12 Hz due to the up-modulation resulting from the Fourier transform. Although decaying weighted filter 90 may reduce the amplitude of the content at 12 Hz, there may be limits to how much decaying weighted filter 90 can reduce the amplitude of the content at 12 Hz. For low-frequency systems, such as system for theta waves, the up-modulated signal content is at a frequency sufficiently close to the frequency component (e.g., 12 Hz is close to 6 Hz) that the low-pass filtering capabilities of decaying weighted filter 90 may be insufficient to remove the up-modulated signal content.

As illustrated in FIG. 5, frequency component phase detector 86 may include correction unit 96. Correction unit 96 may be configured to remove the effects of the signal content from the up-modulated signal.

There may be various ways for correction unit 96 to remove the effects of the signal content from the up-modulated signal. One example way is using a notch filter to the initial estimate phase of the frequency component. Another example way is using an analytical correction term to the initial estimate phase of the frequency component. There may be other ways in which to remove the effect of the up-modulated signal, and the techniques should not be considered limited to the above examples.

The notch filter to remove the up-modulated signal may function well in examples where there is large separation between the up-modulated signal and the frequency component. For low-frequency cases, such as theta wave, there may not be sufficient separation between the up-modulated signal and frequency component. However, it may still be possible to utilize a notch filter even for low frequency applications.

In the examples described in this disclosure, correction unit 96 may implement an analytical correction term, and output phase corrected value (e.g., $\theta_{corrected}$) represents the phase of the frequency component for which frequency component phase detector 86 is configured. In general, the output of correction unit 96 may be a function of θ and $(f_{sr}/f)*(1-r)$. As one example, correction unit 96 may implement the following equation:

$$\theta_{corrected}=\theta-Q*\cos(2*(\theta+Q)) \quad \text{(equation 5)}.$$

In equation 5, "Q" equals $k*(f_{sr}/f)*(1-r)$. The variable "k" is a constant, "$f_{sr}$" is the sampling frequency, "f" is the resonator frequency (e.g., the frequency component for which frequency component phase detector 86 is configured), and "r" is radius of the resonator poles (e.g., the value that determines the rate of decay of the weighting).

However, equation 5 is one example of how correction unit 96 may remove the effects of the signal content from the up-modulated signal. In some examples, correction unit 96 may implement the following equation:

$$\theta_{corrected}=\theta-Q*\cos(2*(\theta+Q))+O(\theta) \quad \text{(equation 5')}.$$

In equation 5', "Q" is the same as in equation 5. The variable "O(θ)" is an error in the correction step. The model may be accurate for Q<<1. For instances where Q is larger, the correction step of correction unit 96 may be implemented using a piece-wise-linear model based on a lookup table formed by observing phase error as a function of input phase at the resonant frequency. For the theta waves described in this disclosure, it may be possible to neglect O(θ).

The examples illustrated in FIGS. 3 and 5 may result in a bandpass shape that is more general than the leaky resonator bandpass shape outputted only by decaying weighted filter 90. For example, as indicated in FIG. 3 and illustrated in FIGS. 4A and 4B, the resonator frequencies of each of frequency component phase detectors 86A-86C summed together provides the a constructed band with a more general bandpass shape without affecting the temporal weighting of the past.

Also, as described above with respect to FIG. 3, the real-time phase of the frequency band may be a weighted phase output average of the outputs of each of the leaky resonators (e.g., outputs of each of frequency component phase detectors 86A-86C). As illustrated in FIG. 5, the frequency weight is based on a product, by multiplier 99, of the weight factor (e.g., "wf" used to form the more ideal band of creating unity gain across the band, as described above with respect to FIG. 3 and illustrated in FIGS. 4A and 4B) and the amplitude of the output of decaying weighted filter 90 (e.g., leaky resonator output amplitude).

The amplitude of the output of the leaky resonator (e.g., output of decaying weighted filter 90) is the magnitude of the phasor output as the output of the leaky resonator is low pass filtered. For example, as illustrated in FIG. 5, low pass filter 98 receives the output from decaying weighted filter 90 (e.g., the filtered signal represented by phasor X+jY) and low-pass filters the output with a single pole filter that is multiplied by the magnitude of the complex phasor. Low pass filter 98 may be configured to implement the following transfer function:

$$\text{sqrt}(X^2+Y^2)/(1-rz^{-1}).$$

In some examples, passing the output of decaying weighted filter 90 through low pass filter 98, which implements the above transfer function, may be useful in measuring the phase of an EEG, such as the theta wave (but may not be needed for other types of signals or other frequency bands). In some cases, an EEG oscillation may vary within a frequency range (e.g., 4 Hz to 8 Hz for the theta wave). Without the constructed idealized frequency band based on the weight factor, as described above, with respect to FIGS. 3 and 4, when the input frequency moves away from peak resonance, the recent past is weighted less heavily than the more distant past, resulting in a sluggish phase-change response. The bandpass shape may be optimized for patients and signal origin by simple parametric adjustment. For example, amplitude gain is less when frequency is off of the resonance (e.g., off of the respective frequencies for which each of frequency component phase detectors 86A-86C are configured. Accordingly, when the input signal is away from resonance, the input signal may not contribute as much to the calculation compared to earlier portions of the signal, and frequency band phase detector 78 may be slower to response to recent changes in the signal.

Accordingly, in the example illustrated in FIG. 5, decaying weighted filter 90 filters the input signal by correlating (e.g., comparing) the input signal to one or more (e.g., two or more) different phase shifted (e.g., delayed) versions of a representative pattern. For example, decaying weighted filter 90 utilized sine and cosine waves whose frequency is the frequency component to correlate the input signal. The relative correlation of the input signal with the representative patterns may determine the pattern's phase (e.g., a noisy phase of the frequency component that includes the phase of the frequency component and a phase error). The phase error is due to the differing delays of frequencies through decaying weighted filter 90. In this example, more recent past portions of the signals is use more heavily than the more distant past in estimating the phase because the more recent past portions are more indicative of the present phase.

The differing delays of frequencies through decaying weighted filter 90 (e.g., differing delays of the different frequency components of the signal) is corrected by correlating the input signal to this noisy phase estimate (e.g., $\theta_1$) of the representative pattern (and a delayed version) thereby measuring the filter delay (e.g., phase error) used to obtain the actual phase from this noisy phase estimate. For example, correlation unit 91 correlates the input signal with the output of decaying weighted filter 90, and the output of correlation unit 91, and in some examples, after filtering through integrator 92 is a signal whose phase is equal to the phase error (e.g., $\theta_2$). Subtractor 95 subtracts $\theta_2$ from $\theta_1$ to determine an initial estimate of the phase of the frequency component, and correction unit 96 removes up-modulated portion of the filtered signal to output the phase of the frequency component.

In this disclosure, one possible representative pattern is cosine where the above approach can be referred to as a Fourier transform with predominantly decreasing weighting of the past where the filter delay (e.g., phase error) can be accounted for by correlating the input signal with the Fourier transform's result (e.g., via correlation unit 91), obtaining the actual real-time phase. The techniques described in this disclosure may be replicated and combined over a wider distribution of representative patterns encompassing a broader range of input signal components.

FIG. 6 is a flowchart illustrating a method in accordance with one or more example techniques described in this disclosure. As illustrated in FIG. 6, one or more frequency component phase detectors (e.g., frequency component phase detectors 86A-86C) may determine phases for each of one or more frequency components of a frequency band of a first signal (e.g., 4 Hz, 6 Hz, and 8 Hz of a theta wave of a bioelectrical brain signal), where determining the phases for each of the one or more frequency components of the frequency band of the first signal includes weighting present and more recent portions of the first signal more heavily than earlier portions of the signal (100). In some examples, the first signal may be generated from a second signal (e.g., notch filter 84 may receive the second signal, which is a sensed signal, and pre-filter the second signal to generate the first signal). There may be other ways in which the second signal (e.g., sensed signal) is pre-filtered, and the disclosure is not limited to notch filter 84 pre-filtering. In some examples, where notch filter 84 is not utilized or there is no other pre-filtering, the second signal may be the same as the first signal (e.g., the frequency component phase detectors 86A-86C receive the sensed signal without pre-filtering).

Each one of frequency component phase detectors 86A-86C may determine phases for respective frequency components of the first signal by correlating the first signal with respective frequency components of the frequency band of the first signal by weighting present and more recent portions of the first signal more heavily than earlier portions of the first signal. For example, each one of frequency component phase detectors 86A-86C may correlate the first signal (e.g., one outputted by notch filter 84 in examples where notch filter 84 is used) with waveforms of a periodic basis set (e.g., sine and cosine waves as used in a Fourier transform) with a predominantly decaying weighting of the first signal.

Frequency band phase detector 78 may determine a phase of the frequency band of the second signal used to generate the first signal based on the determined phases for each of the one or more frequency components (102). For example, averager 88 may determine a weighted average based on a frequency weight for each respective frequency component and the phase for each respective frequency component, and the phase of the frequency band may equal the result of the weighted average. In some examples, averager 88 or each one of frequency component phase detectors 86A-86C may add or subtract respective phase delays, caused by the pre-filtering (e.g., by notch filter 84), for respective frequency components to the determined phases for each of the one or more frequency components of the frequency band of the first signal. Averager 88 may determine the phase of the frequency band of the second signal based on the result of the adding or subtracting. For example, averager 88 may determine a weighted average based on a frequency weight for each respective frequency component and the phase, resulting from the adding or subtracting of respective phase delays, for each respective frequency component, and the phase of the frequency band may equal the result of the weighted average.

FIG. 7 is a flowchart illustrating a method in accordance with one or more example techniques described in this disclosure. As illustrated in FIG. 7, frequency band phase detector 78 may receive a first signal generated from a second signal (104). In one example, the second signal may be a sensed signal that is pre-filtered (e.g., by notch filter 84) to generate the first signal. However, there may be other ways in which the second signal is pre-filtered (including the case where there is added delay from the traveling of the second signal on a circuit). In one example, the first signal and the second signal may be the same signal (e.g., where notch filter 84 or other pre-filtering is not employed). This second signal includes a frequency band, which includes one or more frequency components (e.g., the second signal is a sensed brain signal that includes the theta frequency band, which includes one or more frequency components such as 4 Hz, 6 Hz, and 8 Hz).

At least one frequency component phase detector 86A-86C may correlate the first signal with a frequency component of the frequency band of the second signal by predominately (e.g., generally) decreasing weighting of past portions (e.g., samples) of the first signal, where predominately decreasing weighting of past portions of the first signal includes predominately weighting present and more recent portions of the first signal more heavily than earlier portions of the first signal (106). The decreasing weighting results in portions of the first signal that are closer in time to the point of the second signal for which the phase is being determined having greater effect in determining the phase than the effect of portions of the first signal that are further away in time to the point of the second signal for which the phase is being determined. Such decreasing weighting may be beneficial because more recent samples are more predictive of the phase than less recent samples, and if all samples were equally weighted the less predictive samples would contribute to determining the phase as much as the more predictive samples, resulting in a less accurate phase determination. By weighting more predictive samples more heavily, the techniques may more accurately determine phase.

In one example, correlating the first signal with the frequency component of the frequency band of the second signal by predominantly decreasing weighting of past portions of the first signal includes correlating the first signal with one or more waveforms of a periodic basis set. The frequency of the waveforms of the periodic basis set is the frequency component. As one example, the waveforms of the periodic basis set include a sine wave and a cosine wave. For instance, correlating the first signal with the frequency component of the frequency band of the second signal by predominantly decreasing weighting of past portions of the first signal includes Fourier transforming the first signal with an exponentially decreasing weighting of past portions of the first signal.

At least one frequency component phase detector 86A-86C may determine a phase of the frequency component based on a filtered signal outputted from the correlation (108). For example, the output of decaying weighted filter 90 (represented as a complex phasor output X+jY) is a filtered signal, and frequency component phase detector 86 may determine the phase of the frequency component based on the output of decaying weighted filter 90. Phase determination 94A may determine a phase of the filtered signal outputted from decaying weighted filter 90 (e.g., a tan (Y/X). The phase of the filtered signal is a noisy estimate of the phase because the phase of the filtered signal includes the phase of the frequency component and a phase error. The phase error includes the unaccounted for phase delay which varies for each of the frequencies in the signal and the phase delay of the frequency component caused by decaying weighted filter 90.

Frequency component phase detector 86 may determine the phase error, and subtract, via subtractor 95, the determined phase error, via phase determination unit 94B, from the phase of the filtered signal, via phase determination unit 94A, to determine an initial phase of the frequency component. Correction unit 96 may apply at least one of a notch filter or a correction term to the initial phase of the frequency component, and the result may be the phase of the frequency component. In this manner, frequency component phase detector 86 may determine the phase of the frequency component based on the application of at least one of the notch filter or the correction term to the initial phase of the frequency component.

There may be various ways in which frequency component phase detector 86 may determine the phase error. As one example, frequency component phase detector 86 may implement a self-correlation (self-modulation) scheme. For instance, correlation unit 91 may correlate the first signal (e.g., the received signal) with the filtered signal (e.g., the output of decaying weighted filter 90). Integrator 92 may low-pass filter a signal resulting from the correlation (e.g., low-pass filter the output of correlation unit 91) to generate a filtered correlated signal, represented as the complex phasor $X_2+jY_2$. Phase determination unit 94B may determine a phase of the filtered correlated signal. In this example, the phase error may be the determined phase of the filtered correlated signal.

Frequency band phase detector 78 may determine a phase of the frequency band based on the determined phase of the frequency component (110). For example, averager 88 may receive the phase for each of the respective frequency components from respective frequency component phase detectors 86A-86C. Averager 88 may determine a weighted average of the received phases to determine the phase of the frequency band.

In examples where there is pre-filtering of the second signal (e.g., sensed signal) to generate the first signal that is received by frequency component phase detectors 86A-86C, the pre-filtering may cause a phase delay for each respective frequency component, and the phase delay may not be uniform (e.g., may be different for each frequency component). In some examples, averager 88 may add or subtract a phase delay caused by generating the first signal from the second signal to the determined phase of the frequency component. However, rather than averager 88 adding or subtracting the phase delay, respective ones of frequency component phase detectors 86A-86C may add or subtract this phase delay (or some combination of both averager 88 and frequency component phase detectors 86A-86C). Averager 88 may determine the phase of the frequency band based on the result of the adding or subtracting. For example, averager 88 may determine the weighted average on the result of the adding or subtracting to determine the phase of the frequency band.

In some examples, in addition to the respective phases, each of frequency component phase detectors may be configured to determine respective frequency weights. The frequency weights may be based on a weight factor multiplied by a low pass filtered output of decaying weighted filter 90 multiplied by the magnitude of the output of decaying weighted filter 90. For instance, the amplitude of the filtered signal (e.g., the amplitude of the output of decaying weighted filter 90) is determined by calculating the magnitude of the filtered signal (e.g., sqrt ($X^2+Y^2$)) and passing it through a single pole low pass filter (e.g., low pass filter 98). Multiplier 99 multiples the weight factor with the output of low pass filter 98. In such examples, averager 88 may be configured to determine the phase of the frequency band based on a weighted average of the determined phases (or the phases resulting from the adding or subtracting of respective phase delays from pre-filtering) and frequency weights of respective frequency components.

The output of frequency band phase detector 78 is the phase of the frequency band. The phase of the frequency band may be used for various purposes. As one example, IMD 16 may deliver therapy based on the determined phase of the frequency band. For example, processor 60 may instruct therapy module 65 to deliver therapy based on the determined phase of the frequency band. As another example, IMD 16 may determine information used to diagnose based on the determined phase of the frequency band.

Figure 8:
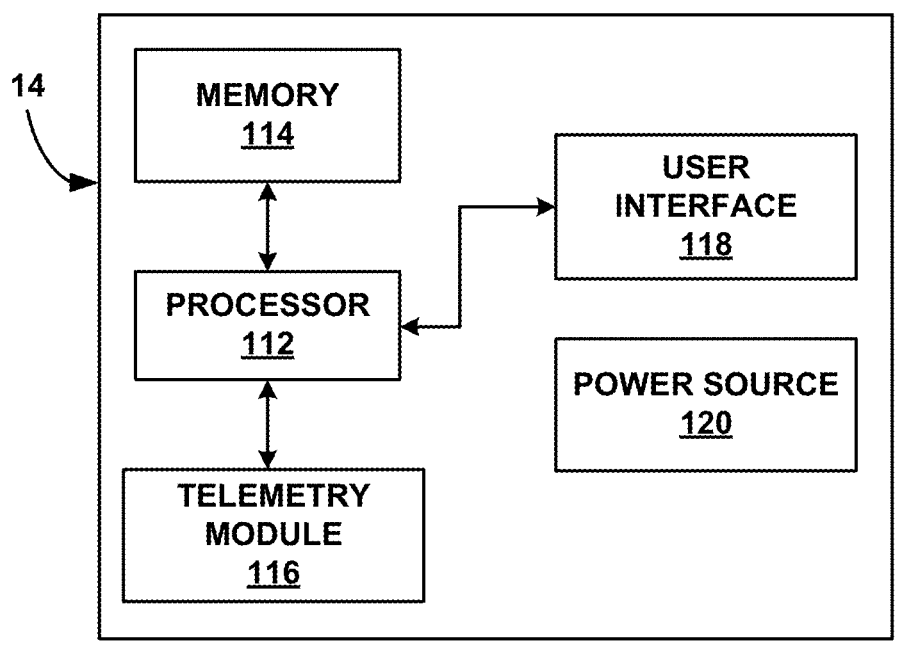
FIG. 8 is a functional block diagram illustrating components of an example medical device programmer.

FIG. 8 is a functional block diagram illustrating components of an example medical device programmer 14 (FIG. 1). Programmer 14 includes processor 112, memory 114, telemetry module 116, user interface 118, and power source 120. Processor 112 controls user interface 118 and telemetry module 116, and stores and retrieves information and instructions to and from memory 114. Programmer 14 may be configured for use as a clinician programmer or a patient programmer. Processor 112 may comprise any combination of one or more processors including one or more microprocessors, DSPs, ASICs, FPGAs, or other equivalent integrated or discrete logic circuitry. Accordingly, processor 112 may include any suitable structure, whether in hardware, software, firmware, or any combination thereof, to perform the functions ascribed herein to processor 112.

A user, such as a clinician or patient 12, may interact with programmer 14 through user interface 118. User interface 118 includes a display (not shown), such as a LCD or LED display or other type of screen, with which processor 112 may present information related to the therapy, a patient condition detected by programmer 14 or IMD 16 based on a frequency domain characteristic of a sensed bioelectrical brain signal, or electrical signals sensed via a plurality of sense electrode combinations. In addition, user interface 118 may include an input mechanism to receive input from the user. The input mechanisms may include, for example, buttons, a keypad (e.g., an alphanumeric keypad), a peripheral pointing device or another input mechanism that allows the user to navigate through user interfaces presented by processor 112 of programmer 14 and provide input.

If programmer 14 includes buttons and a keypad, the buttons may be dedicated to performing a certain function (i.e., a power button), or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 118 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 112 of programmer 14. For example, in some examples, processor 112 may receive sensed brain signal information from IMD 16 or from a sensing module that is separate from IMD 16. The separate sensing module may, but need not be, implanted within patient 12. Brain signal information may include, for example, a raw bioelectrical brain signal, parameterized bioelectrical brain signal, or any other suitable information indicative of a bioelectrical brain signal sensed by sensing module 66. For example, processor 112 may receive phase information indicating the phase of the frequency band of interest, and may utilize the information for purposes of diagnosing patient 12 or may utilize the information to present the instantaneous phase of the frequency band. In some examples, rather than IMD 16, processor 112 may add a known phase shift to align the phase with the bioelectrical brain signal.

Memory 114 may include instructions for operating user interface 118 and telemetry module 116, and for managing power source 120. In some examples, memory 114 may also store any therapy data retrieved from IMD 16 during the course of therapy, sensed bioelectrical brain signals, and the like. In some instances, the clinician may use this therapy data to determine the progression of the patient condition in order to plan future treatment for the movement disorder (or other patient condition) of patient 12. Memory 114 may include any volatile or nonvolatile memory, such as RAM, ROM, EEPROM or flash memory. Memory 114 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 116. Accordingly, telemetry module 116 may be similar to the telemetry module contained within IMD 16. In some examples, programmer 14 may be capable of infrared communication or direct communication through a wired connection. In this manner, other external devices may be capable of communicating with programmer 14 without needing to establish a secure wireless connection.

Power source 120 is configured to deliver operating power to the components of programmer 14. Power source 120 may include a battery and a power generation circuit to produce the operating power. In some examples, the battery may be rechargeable to allow extended operation. Recharging may be accomplished by electrically coupling power source 120 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

In some examples, it may be possible for programmer 14 to perform the phase detection techniques of IMD 16. For example, IMD 16 may offload the phase detection process to programmer 14. As an example, processor 112 of a medical device (e.g., programmer 14, in this case) may receive a first signal generated from a second signal (e.g., receive from IMD 16). Processor 112 may correlate the first signal with a frequency component of a frequency band of the second signal. The correlating includes predominantly decreasing weighting of past portions of the first signal, and predominantly decreasing weighting of past portions of the first signal includes predominantly weighting present and more recent portions of the first signal more heavily than earlier portions of the first signal, and the frequency band includes one or more frequency components. Processor 112 may determine a phase of the frequency component based on a filtered signal outputted from the correlation, determine a phase of the frequency band based on the determined phase of the frequency component, and instruct a therapy module (e.g., therapy module 65 of IMD 16) to deliver therapy based on the determined phase of the frequency band.

In some cases, instead of therapy delivery, programmer 14 may utilize this determined phase for other purposes such as providing information for diagnosing. There may be various uses for the determined phase of the frequency band and therapy delivery and diagnosing patient are two of the various examples. Also, processor 60 may be configured to determine the phase of the frequency band, and may use this information to control therapy by therapy module 65 (e.g., instruct therapy module 65 to deliver therapy) or output this information for assisting a clinician with diagnosis, or possibly for various other reasons where knowing the phase of the frequency band is useful.

The following describes some examples comparing the results of real-time phase detection techniques described in this disclosure and non-real-time phase detection techniques. To test the performance of the EEG theta wave application of this method, sheep EEG data was studied to determine expected noise characteristics, theta frequency range, and degree of frequency and amplitude modulation of the theta wave. A more limited set of human EEG data was also studied. Artificial (and intentionally highly method stressing) EEG waveforms were generated to gain insight into the performance. Also, a real sheep EEG waveform strip with known theta content was tested to validate and supplement this study. In the generated waveforms, the frequency modulations are 2 Hz peak to peak and have a period of 2 seconds. The center of the modulated frequency is swept from 5 hz to 7 hz to 5 hz over a 20 second period. The noise injected is 1/f noise. The signal/noise energy levels are 0.5857 with respect to content contained within the non-real-time method bandpass filter described below.

Figure 9:
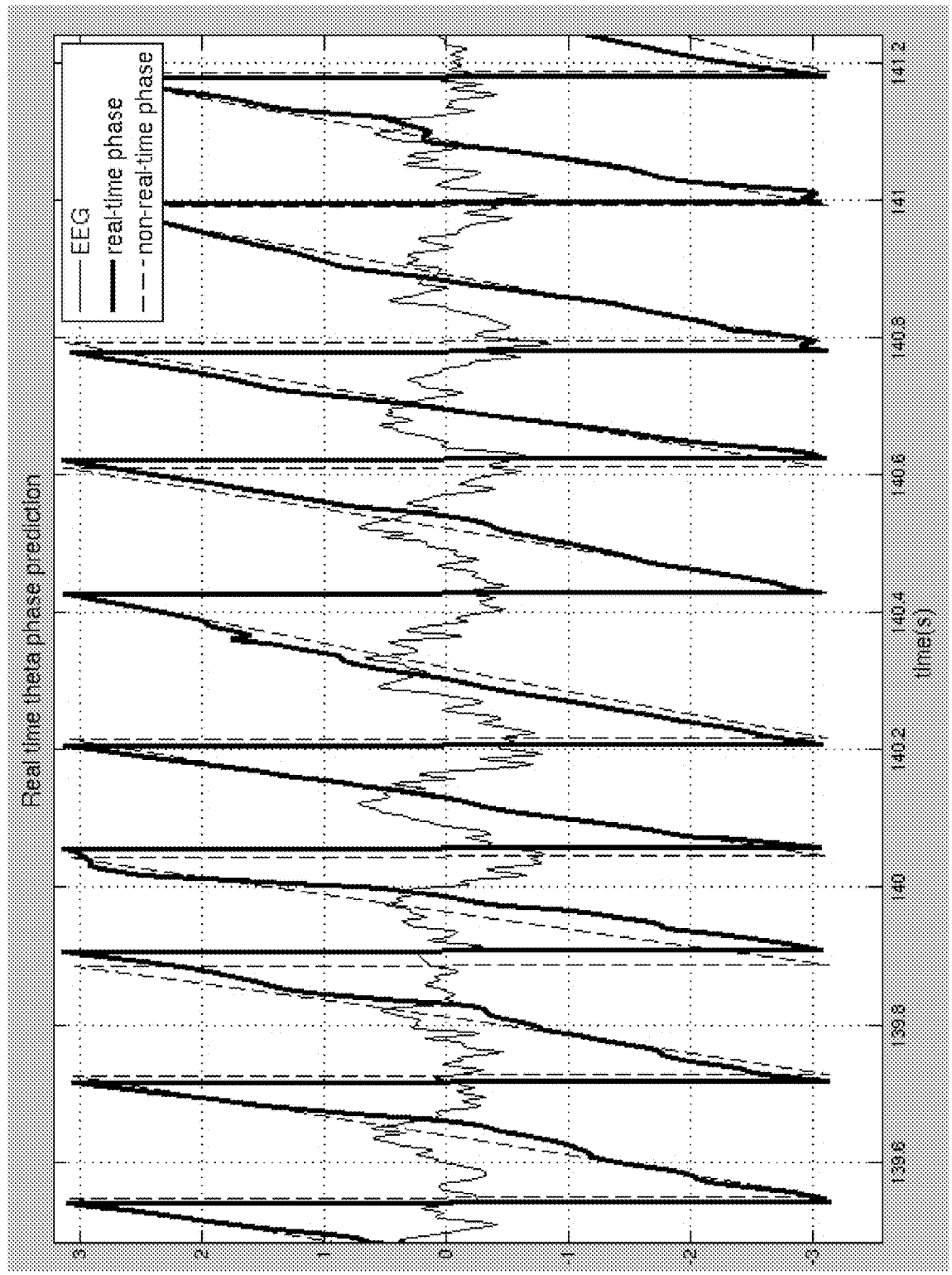
FIG. 9 is a graph illustrating a comparison of results between real-time phase detection techniques described in this disclosure and non-real-time phase detection techniques.
Figure 10:
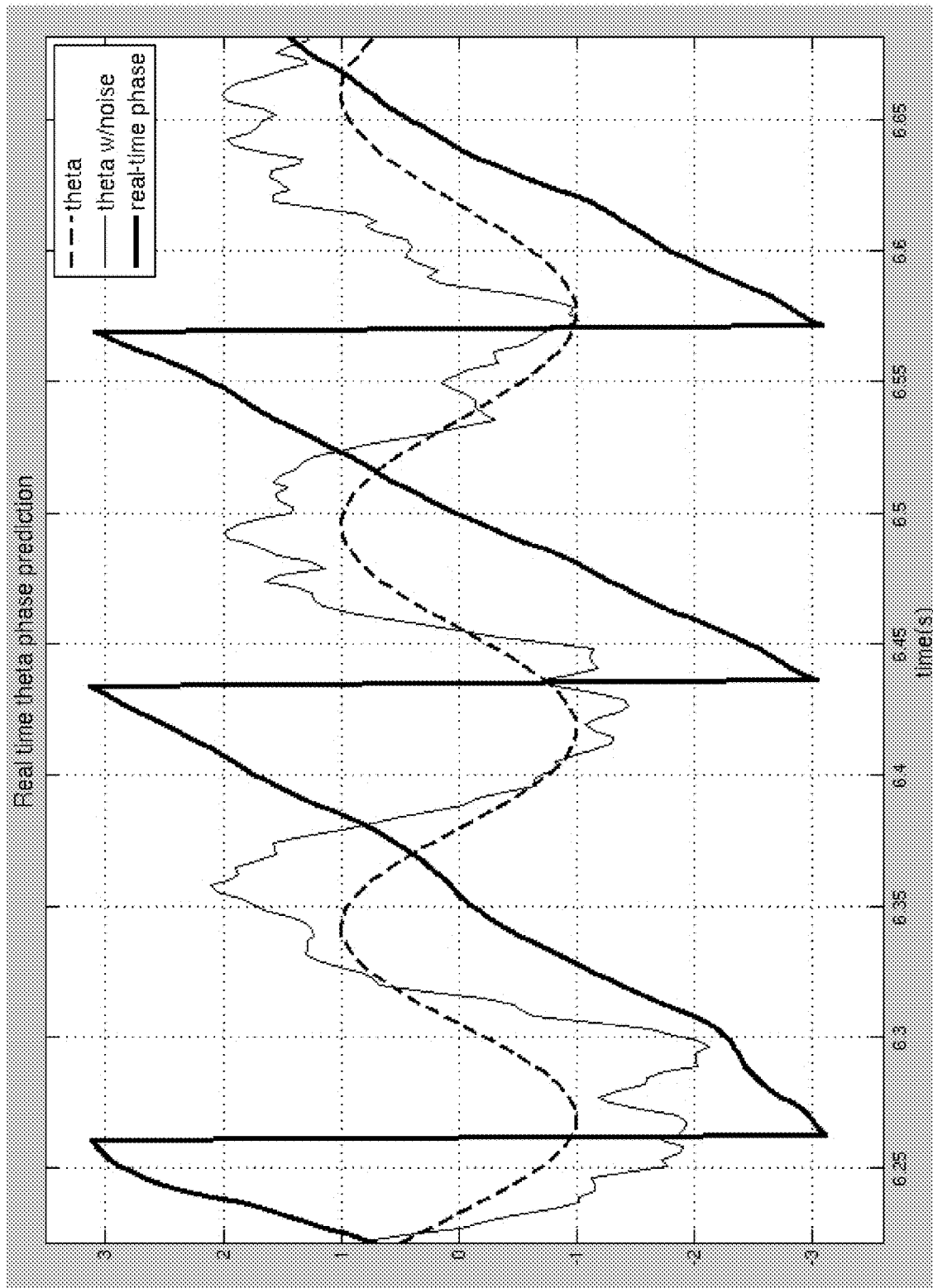
FIG. 10 is a graph illustrating another comparison of results between real-time phase detection techniques described in this disclosure and non-real-time phase detection techniques.

The non-real-time approach was implemented for comparison purposes. It was accomplished by forward and reverse filtering the data with a Gaussian windowed bandpass filter, resulting in a Gaussian frequency response centered at 6 hz with a standard deviation of 2.1 Hz and zero delay. Finally, a Hilbert transform ($\pi/2$ phase shift) is applied to the data to get the imaginary component of the corresponding complex phasor. The real-time phase is calculated from the angle (phase) of the complex phasor. The actual phase in the absence of noise is known in the generated EEG data and provides another comparison point. Tables 2 and 3 below show the RMS phase error between the real-time method/actual phase, non-real-time method/actual phase, real-time method/non-real-time method, and extra RMS phase error resulting from not having access to future EEG waveform data (i.e., the real-time penalty). Performance on a strip of real sheep EEG data with known theta content is also provided in the tables.

this disclosure and non-real-time phase detection techniques. FIG. 10 is a graph illustrating another comparison of results between real-time phase detection techniques described in this disclosure and non-real-time phase detection techniques. FIGS. 9 and 10 show phase estimation performance for the sheep EEG and row 6 of Table 2, respectively. The reported phase is shifted by a fixed amount to have $\pi$ align with the trough of the theta wave, increasing observability. In FIG. 9, the sheep EEG, row 7 of Table 2 is illustrated, with the plot showing the theta wave phase of sheep EEG determined by real-time and non-real-time methods. The measured phase determined by the non-real-time method is shown for comparison. In FIG. 10, the theta way phase detection on a simulated EEG trace is illustrated, swept in frequency, frequency modulated, and with 1/f noise added to the signal to highly stress the method.

The above examples are for computationally efficient techniques for a real-time phase detector. The techniques utilize a real-time Fourier transform (RTFT) (e.g., frequency component phase detectors 86A-86C) by utilizing a normal Fourier transform with a predominantly decreasing weighting of the past and zero weighting of the future. The predominantly decreasing weighting of the past may be used for its predictive capability of the present. However, using an asymmetric weighting function (window) may result in non-linear phase delay. This is why classical spectral esti-

TABLE 2

RMS error in EEG theta wave phase measurement

| | rms_error(real-time vs. non-real-time) | rms_error(real-time vs. actual) | rms_error(non-real-time vs. actual) | rms_error(extra error for real-time) |
|---|---|---|---|---|
| 6 hz sine | 0.0090*$\pi$ | 0.0090*$\pi$ | 0.0007*$\pi$ | 0.0090*$\pi$ |
| Only 1/f noise | 0.3511*$\pi$ | NA | NA | NA |
| Only swept f | 0.0137*$\pi$ | 0.0130*$\pi$ | 0.0019*$\pi$ | 0.0110*$\pi$ |
| Swept f and FM(4-8 hz) | 0.0651*$\pi$ | 0.0505*$\pi$ | 0.0194*$\pi$ | 0.0311*$\pi$ |
| 6 hz sine + 1/f noise | 0.1685*$\pi$ | 0.2119*$\pi$ | 0.1027*$\pi$ | 0.1092*$\pi$ |
| Swept FM(4-8 hz), 6 hz sine + 1/f noise | 0.2063*$\pi$ | 0.2336*$\pi$ | 0.1560*$\pi$ | 0.0777*$\pi$ |
| Sheep EEG | 0.1279*$\pi$ | NA | NA | NA |

TABLE 3

RMS error in EEG theta wave phase measurement updated
(Comparison (std. dev. rems error in radians)

| Simulation | rms_error(real-time vs. non-real-time) | rms_error(real-time vs. actual) | rms_error(non-real-time vs. actual) | rms_error(Diff real-time vs. non-real-time) |
|---|---|---|---|---|
| Only 1/f noise | 0.36*$\pi$ | | | |
| 6 Hz sine | 0.023*$\pi$ | 0.023*$\pi$ | 0.0007*$\pi$ | 0.023*$\pi$ |
| 6 Hz sine, AM | 0.040*$\pi$ | 0.041*$\pi$ | 0.0061*$\pi$ | 0.035*$\pi$ |
| Sweep & FM | 0.069*$\pi$ | 0.055*$\pi$ | 0.019*$\pi$ | 0.037*$\pi$ |
| 6 hz sine + 1/f noise | 0.13*$\pi$ | 0.15*$\pi$ | 0.069*$\pi$ | 0.084*$\pi$ |
| AM + 1/f noise | 0.27*$\pi$ | 0.34*$\pi$ | 0.24*$\pi$ | 0.097*$\pi$ |
| Sweep, FM + 1/f noise | 0.17*$\pi$ | 0.19*$\pi$ | 0.11*$\pi$ | 0.078*$\pi$ |

FIG. 9 is a graph illustrating a comparison of results between real-time phase detection techniques described in mation techniques use symmetric windows. The techniques recover from this non-linear phase delay by measuring this phase delay by modulating the input and output of the weighted Fourier transform. The measured phase error is then subtracted from the result of the weighted Fourier transform. As with a normal Fourier transform, there is a tradeoff between frequency and time resolution. The potential application space for the developed RTFT concept and other implementations of it is considerably more extensive than real-time EEG band phase detection. The EEG band phase detection is provided as one example. The techniques also combine multiple RTFTs (e.g., frequency component phase detectors 86A-86C) to form an optimal band shape and calculate the resulting real-time phase for this optimal band (e.g., via averager 88).

Even under extreme noise and modulation conditions (i.e. frequency and amplitude modulation), the real-time performance with respect to the non-real time method produces a tight distribution with less than a 3% or ~10° bias and approximately 4% or 15° standard deviation. This suggests that the techniques are both robust and accurate under a range of conditions.

Furthermore, implementing the example techniques may require only a few mathematical operations per sample, and given typical implantable device 90 nanometer (nm) silicon technology operating at 0.85V, the implementation of the techniques may consume less than 1 µW of power and cover less than a 500 µm×500 µm area. This estimate assumes 16 bit data at 250 Hz, using time shared functions, with trigonometric functions implemented by a sea-of-gates lookup table. Moreover, this phase detection method can report the real-time phase at a high data rate (e.g., at the incoming data sampling rate), reducing or effectively eliminating latency in computing the real-time phase.

There have been earlier efforts to achieve real-time phase detection, but none have achieved the combination of accuracy and computational efficiency needed for implantable, wearable, or portable applications. For example, some techniques utilize a powerful algorithm based on autoregression and employed genetic algorithms to search for optimal parameters. The algorithm may require intensive computational power not appropriate for implantable devices with reduced instruction set processors, limited memory, and extreme power restrictions. Furthermore, since the band pass filter in this previous approach uses a symmetric window, it underweights the most recent, most predictive data. However, the techniques described in this disclosure utilize an asymmetric window to properly weigh more recent samples.

Some earlier techniques present an adaptive method of frequency tracking that is used for phase detection and phase-phase coupling. However, such earlier techniques would not function well for real-time phase detection and therefore are not specifically optimized for computational efficiency (i.e., each time step involves many multiplication, addition, and averaging operations). The computational intensity of such techniques further increases with extension to multiple-signal tracking.

While the techniques described above are primarily described as being performed by processor 60 of IMD 16 or processor 112 of programmer 14, in other examples, one or more other processors may perform any part of the techniques described herein alone or in addition to processor 60 or processor 112. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
  receiving, with circuitry of a medical device, a first signal generated from a second signal;
  correlating, with the circuitry of the medical device, the first signal with a set of frequency components of a frequency band of the second signal in order to generate a filtered signal, wherein correlating the first signal with the set of frequency components comprises:
    correlating the first signal with a set of waveforms of a periodic basis set, wherein each waveform of the set of waveforms corresponds to a respective frequency component of the set of frequency components such that a frequency of each waveform of the set of waveforms of the periodic basis set is the respective frequency component of the set of frequency components, and
    weighting relatively more recent portions of the first signal more heavily than relatively less recent portions of the first signal as part of correlating the first signal with the set of waveforms of the periodic basis set;
  determining a phase of the frequency band based on the filtered signal;

instructing, with the circuitry of the medical device, a therapy module to deliver therapy based on the phase of the frequency band; and delivering, with the therapy module, the therapy.

2. The method of claim 1, further comprising:

identifying, with the circuitry of the medical device, a region of a group of regions based on the phase of the frequency band, wherein the group of regions comprises at least one peak region and at least one trough region, wherein instructing the therapy module to deliver therapy comprises instructing the therapy module to delivery therapy based on the phase of the frequency band and the region of the group of regions.

3. The method of claim 2, wherein instructing the therapy module to deliver therapy comprises instructing the therapy module to deliver electrical stimulation during the at least one peak region, and wherein the phase of the frequency band is about 90 degrees during the at least one peak region.

4. The method of claim 2, wherein instructing the therapy module to deliver therapy comprises instructing the therapy module to deliver electrical stimulation during the at least one trough region, and wherein the phase of the frequency band is about 270 degrees during the at least one trough region.

5. The method of claim 1, wherein determining the phase of the frequency band comprises:

determining, with the circuitry of the medical device, a phase of each frequency component of the set of frequency components based on the filtered signal outputted from the correlation; and determining, with the circuitry of the medical device, the phase of the frequency band based on the phase of each respective frequency component of the set of frequency components.

6. The method of claim 1, wherein the first signal is one of:

the second signal pre-filtered to generate the first signal; or the same as the second signal.

7. The method of claim 1, further comprising:

determining, for each frequency component of the set of frequency components, a frequency weighting based on the filtered signal, wherein determining the phase of the frequency band comprises determining the phase of the frequency band based on a phase corresponding to each frequency component of the set of frequency components and the frequency weighting corresponding to each frequency component of the set of frequency components.

8. The method of claim 1, wherein determining the phase of the frequency band comprises:

adding or subtracting a phase delay caused from generating the first signal from the second signal to the phase of the frequency component; and determining the phase of the frequency band based on a result of adding or subtracting the phase delay.

9. The method of claim 1, wherein the set of waveforms of the periodic basis set include a sine wave and a cosine wave.

10. The method of claim 1, wherein correlating the first signal with the set of frequency components of the frequency band of the second signal further comprises:

Fourier transforming the first signal with an exponentially decreasing weighting of past portions of the first signal.

11. The method of claim 1, further comprising determining a phase of each frequency component of the set of frequency components in real-time, and wherein determining the phase of the frequency band comprises determining the phase of the frequency band in real-time based on the phase of each frequency component of the set of frequency components.

12. A medical device comprising:

a frequency band phase detector comprising:

a frequency component phase detector configured to:

receive a first signal generated from a second signal; and correlate the first signal with a set of frequency components of a frequency band of the second signal in order to generate a filtered signal, wherein to correlate the first signal with the set of frequency components, the frequency component phase detector is configured to:

correlate the first signal with a set of waveforms of a periodic basis set, wherein each waveform of the set of waveforms corresponds to a respective frequency component of the set of frequency components such that a frequency of each waveform of the set of waveforms of the periodic basis set is the respective frequency component of the set of frequency components, and weight relatively more recent portions of the first signal more heavily than relatively less recent portions of the first signal as part of correlating the first signal with the set of waveforms of the periodic basis set;

an averager configured to determine a phase of the frequency band based on the filtered signal; and a therapy module configured to deliver therapy based on the phase of the frequency band.

13. The medical device of claim 12, further comprising circuitry configured to:

identify a region of a group of regions based on the phase of the frequency band, wherein the group of regions comprises at least one peak region and at least one trough region, wherein the therapy module is configured to delivery therapy based on the phase of the frequency band and the region of the group of regions.

14. The medical device of claim 13, wherein the therapy module is configured to deliver therapy by delivering electrical stimulation during the at least one peak region, and wherein the phase of the frequency band is about 90 degrees during the at least one peak region.

15. The medical device of claim 13, wherein the therapy module is configured to deliver therapy by delivering electrical stimulation during the at least one trough region, and wherein the phase of the frequency band is about 270 degrees during the at least one trough region.

16. The medical device of claim 12, wherein the first signal is one of:

the second signal pre-filtered to generate the first signal; or the same as the second signal.

17. The medical device of claim 12, wherein the frequency band phase detector is configured to:

determine, for each frequency component of the set of frequency components, a frequency weighting based on the filtered signal, wherein to determine the phase of the frequency band, the averager is configured to determine the phase of the frequency band based on a phase corresponding to each frequency component of the set of frequency components and the frequency weighting corresponding to each frequency component of the set of frequency components.

18. The medical device of claim 12, wherein at least one of the frequency component phase detector or the averager is configured to add or subtract a phase delay caused from generating the first signal from the second signal to the phase of the frequency component, and wherein the averager is configured to determine the phase of the frequency band based on a result of adding or subtracting the phase delay.

19. The medical device of claim 12, wherein the set of waveforms of the periodic basis set include a sine wave and a cosine wave.

20. A non-transitory computer-readable storage medium comprising instructions that when executed cause one or more processors of a medical device to:
receive a first signal generated from a second signal;
correlate the first signal with a set of frequency components of a frequency band of the second signal in order to generate a filtered signal, wherein the instructions that cause the one or more processors to correlate the first signal with the set of frequency components comprise instructions that cause the one or more processors to:
correlate the first signal with a set of waveforms of a periodic basis set, wherein each waveform of the set of waveforms corresponds to a respective frequency component of the set of frequency components such that a frequency of each waveform of the set of waveforms of the periodic basis set is the respective frequency component of the set of frequency components, and
weight relatively more recent portions of the first signal more heavily than relatively less recent portions of the first signal as part of correlating the first signal with the set of waveforms of the periodic basis set;
determine a phase of the frequency band based on the filtered signal; and
instruct a therapy module to deliver therapy based on the phase of the frequency band,
wherein the therapy module is configured to deliver the therapy.

* * * * *